United States Patent
Holoien et al.

(10) Patent No.: US 9,757,507 B2
(45) Date of Patent: Sep. 12, 2017

(54) CONFIGURABLE CONTROL FOR OPERATING ROOM SYSTEM

(71) Applicant: Karl Storz Imaging, Inc., Goleta, CA (US)

(72) Inventors: Lee D. Holoien, Santa Barbara, CA (US); Hans-Uwe Hilzinger, Tuttlingen (DE); Christoph Hiltl, Bohlingen (DE)

(73) Assignee: Karl Storz Imaging, Inc., Goleta, CA (US)

( * ) Notice: Subject to any disclaimer, the term of this patent is extended or adjusted under 35 U.S.C. 154(b) by 978 days.

(21) Appl. No.: 13/675,489

(22) Filed: Nov. 13, 2012

(65) Prior Publication Data

US 2014/0135648 A1     May 15, 2014

(51) Int. Cl.
| | |
|---|---|
| *A61M 3/02* | (2006.01) |
| *A61B 10/02* | (2006.01) |
| *A61M 1/00* | (2006.01) |
| *A61B 1/00* | (2006.01) |
| *A61B 34/00* | (2016.01) |
| *A61B 17/32* | (2006.01) |
| *A61B 18/12* | (2006.01) |
| *A61M 13/00* | (2006.01) |
| *A61B 18/00* | (2006.01) |
| *A61B 17/00* | (2006.01) |

(52) U.S. Cl.
CPC ............. *A61M 3/02* (2013.01); *A61B 1/0005* (2013.01); *A61B 10/02* (2013.01); *A61B 34/25* (2016.02); *A61M 1/0058* (2013.01); *A61M 1/0066* (2013.01); *A61B 17/32002* (2013.01); *A61B 18/12* (2013.01); *A61B 2017/00225* (2013.01); *A61B 2018/00982* (2013.01); *A61B 2217/005* (2013.01); *A61M 13/00* (2013.01); *A61M 2205/505* (2013.01); *A61M 2205/581* (2013.01); *A61M 2205/584* (2013.01)

(58) Field of Classification Search
USPC ........................................................ 600/562
See application file for complete search history.

(56) References Cited

U.S. PATENT DOCUMENTS

| | | | |
|---|---|---|---|
| 5,788,688 | A | 8/1998 | Bauer et al. |
| 7,920,162 | B2 | 4/2011 | Masini et al. |
| 8,069,420 | B2 | 11/2011 | Plummer |
| 2003/0171740 | A1 | 9/2003 | Stiller et al. |
| 2004/0024384 | A1 | 2/2004 | Novak |
| 2005/0283138 | A1* | 12/2005 | Tashiro et al. .................... 606/1 |

(Continued)

OTHER PUBLICATIONS

Stryker Fall/Winter 2010 Newsletter, p. 3.*

(Continued)

*Primary Examiner* — Daniel Cerioni
*Assistant Examiner* — Yasmeen S Warsi
(74) *Attorney, Agent, or Firm* — Whitmyer IP Group LLC

(57) ABSTRACT

An operating room control system that is soft configurable allowing a user to completely configure the control and function of the system. The system includes a touchscreen that provides a video display received from a video endoscope and presents icons on the touchscreen allowing the user to control and interface with the tools/equipment in the operating room as well as hospital systems. The controls, displays, tools, equipment, etc. are configured to be operated from a single centralized platform.

43 Claims, 17 Drawing Sheets

(56) References Cited

U.S. PATENT DOCUMENTS

2011/0193949 A1* 8/2011 Nambakam et al. ........... 348/74

OTHER PUBLICATIONS

Stryker SwitchPoint Infinity 3 Control System.*
Stryker SwitchPoint Infinity 3 Brochure.*
Stryker SwitchPoint Infinity Control System Touchscreens.*
OR 1 (R) Essential Drawings Drawn by: SS Dated: Sep. 9, 2008 13 pages.
OR1(R) Essential—Instruction Manual; (c) 2009 Karl Storz Endoscopy-America, Inc.; 36 pages.

* cited by examiner

CONFIGURABLE CONTROL FOR OPERATING ROOM SYSTEM

FIELD OF THE INVENTION

The invention relates to a system and method for controlling an operating room system, and more specifically the invention relates to a configurable system that allows for a physician to completely configure the control interface(s), display(s) and equipment for an entire operating room environment.

BACKGROUND OF THE INVENTION

A wide variety of operating room systems are known for performing both diagnostic and surgical procedures. In particular, systems have been provided that allow a surgeon to perform a procedure with a wide variety of medical and operating room equipment. This equipment ranges from visual imaging tools (e.g., endoscopes, cameras, etc.) and systems, to medical devices (e.g. tools for cutting, grasping, extracting, irrigating, etc.), and other operating room equipment.

In particular, operating room visualization equipment has been provided that allows for visualization of the interior of an organ or joint while a surgeon is conducting a procedure. These visualization systems allow for a surgeon to view, typically on a surgical monitor placed either in or adjacent to the sterile environment, a location inside the body where the procedure is being performed. These systems have further allowed for the recording of still pictures and video recordings of the area and procedure. Not only have the surgeon and those in the operating room been able to view the surgical site on the surgical monitor, but systems have further provided for the transfer of visualization information via a network connection to remote locations from the operating room. In this manner, individuals have had the capacity to view a surgical procedure from different locations. This has proved to be a very helpful educational tool (e.g. medical students can view a medical procedure from a class room) and has allowed for specialists to view the surgical procedure from a distance to provide expert analysis and input to the surgeon.

Touchscreen control interfaces have also been in wide use in the industry for a number of years for the control of medical equipment including the routing of medical visualization data. For example, U.S. Pat. No. 8,069,420 to Roderick Plummer (the Plummer patent), discloses a system that allows for the identification of video collecting sources and the video destinations such that the surgeon need only select the icon on the touchscreen corresponding to the video input device and select the icon on the touchscreen corresponding to the desired destination and the video is routed to the desired destination.

The Plummer patent was a very large leap over prior art systems in that it allowed the surgeon control via a very user friendly interface, to route medical imaging data by simply selecting the icon on the touch screen.

However, while audio-visual capabilities have continued to be developed and improved, control of the remaining operating room equipment has lagged behind. For example, diverse medical equipment (e.g., medical equipment manufactured by different companies and different manufacturers) continues to be the norm in operating room environments. Some of this equipment, in particular, the visualization equipment, has been integrated with and may be controlled by commands input into a touchscreen controller. For example, selection of video source and destination has been provided on a touchscreen controller as discussed in connection with the Plummer patent, as has the ability for teleconferencing. However, typically, control of many of the other various equipment is required to be performed by an individual (e.g., a nurse or other medical personnel) in the operating room to adjust various pieces of equipment that are positioned outside of the sterile environment acting on instruction from the surgeon. These diverse pieces of medical equipment have not been integrated into the touchscreen control because of the diverse signals and signal formats, control formats and lack of network connections on the diverse equipment manufactured by different companies.

Other systems have provided for integrated control systems that have provided limited control of medical equipment in an operating room. For example, U.S. Pat. No. 5,788,688 to James Bauer et al. (the Bauer et al. patent) teaches a networked system for command and control of operating room equipment in the sterile environment. The Bauer et al. patent also teaches that a surgeon's preset preferences may be uploaded such that the system may be pre-adjusted (within defined parameters) to a surgeon's preferred settings thereby saving time and reducing possible errors in the setting of equipment.

Again, however, while the Bauer et al. patent was a great leap forward in technology in the control of various medical devices, more and more diverse pieces of equipment are being introduced to the operating room that must be controlled. Laparoscopic surgery is a good example where one relatively large array of devices and equipment may be used including: cutting devices (laser, bi-polar, etc.), insufflation devices, suction devices, pumps, irrigation devices and cell collection and storage devices. Each piece of equipment has specific and unique operating parameters that, if not operated uniformly, can lead to serious negative consequences for a patient. While the Plummer patent has provided for some integrated control via an interface positioned in the sterile environment, more and more diverse equipment is being added to the operating room environment. It is important that this new and diverse equipment be put under direct control of the surgeon to avoid any mis-adjustments due to miscommunication or error on the part of the personnel adjusting the equipment.

The present invention is directed to solving one or more of the problems discussed above.

SUMMARY OF THE INVENTION

Accordingly, it is an object of the present invention to provide a fully integrated operating room system that provides for complete control of operating room equipment both in and out of the sterile environment.

It is a further object of the present invention to provide an operating room system that allows for control of medical visualization devices, control for medical tools and control of essentially all of the equipment in the operating room environment from an interface in the sterile environment.

It is another object of the present invention to provide an operating room system that is soft configurable, such that the interface placed in the sterile environment that is used to control the entire operating room system is fully customizable in accordance with a surgeon's preferences.

It is still another object of the present invention to provide a fully customizable interface that presents a customized checklist of procedures to be followed for a specified procedure in accordance with a surgeon's preferences.

In accordance with aspects of the invention, an operating room control system is provided that allows for complete control of operating room equipment located both in and out of the sterile environment. For example, a fully integrated system that provides for control of medical visualization devices, control for medical tools and control of essentially all of the equipment in the operating room environment from an interface in the sterile environment is provided.

The operating room control system may comprise a computer having a network connection, an operating room system interface coupled to the computer, a storage accessible by the computer for storing medical images, an endoscope generating a video output coupled to the network interface, at least one medical tool coupled to the network interface, a plurality of medical equipment coupled to the network interface, operating room equipment coupled to the network interface, a touchscreen coupled to the network interface, a surgical monitor coupled to the network interface, wherein icons associated with the endoscope, the at least one medical tool and the plurality of medical equipment are displayed on the touchscreen, and wherein the video output is displayed on the touchscreen, and wherein the system is soft configurable such that icons representative of the endoscope, the medical tool, the plurality of medical equipment, and the operating room equipment are displayed on the touchscreen in a manner selected by the user and the video output and retrieved medical images are displayed on the touchscreen and surgical monitor in a manner selected by the user.

The term "soft configurable" as used herein means that the system is completely configurable based on the user's (surgeon's) preferences. For example, the surgeon may desire to have the video output from the endoscope be displayed in the top center of the touchscreen and on the surgical monitor and when medical images (x-ray, MRI, etc.) are retrieved, the surgeon may have the medical image be displayed at the bottom center of the touchscreen and further it may be overlaid on a portion of the surgical monitor. In any event, the location and positioning, size and brightness and so on, of the image is controlled by the surgeon's preferences. Likewise, the positioning of the icons is controlled by the surgeon's preferences. For example, the surgeon may desire the control interfaces (icons) for the endoscope and the medical tool(s) (catheterization, cutting tools, cell collection, suction devices, etc.) be located on the left side of the touchscreen and the control interfaces (icons) for the plurality of medical equipment (insufflation, irrigation pumps, vacuum sets, etc.) and the operating room equipment (lights, blinds, table, etc.) be positioned on a right side of the touchscreen. While examples of medical tools, medical equipment and operating room equipment are provided, these are not meant to be limiting as additional icons may be provided on the touchscreen as desired by the user that could include destinations for video data to be saved and routed to. For example, the user may desire to save some or all of the video data generated by the endoscope to the storage device. The storage device icon can be placed anywhere convenient for the user such that touching the endoscope icon could activate the video endoscope to begin generating video data displayed in a manner specified by the user, then touching the storage icon positioned in a manner desired can begin routing the video data to the storage device to be saved, and touching the storage icon a second time can pause or interrupt the saving of the video stream. It is further contemplated that the icon can change during activation or interruption (e.g., the endoscope icon can be changed to a "green" color when generating video data or to a "red" color when interrupted). Likewise, the storage icon can change color when data is being written to the storage device.

While only one "storage" has been discussed above, it should be understood that numerous storage devices may be used including, but not limited to, an solid state hard drive, a magnetic hard drive, optical devices, a removable storage device (DVD, thumb drive, etc.), and the storage can be positioned locally or over a network connection such as the Internet. For example, the user could set up the touch screen such that a local hard drive, a remote hard drive and a removable storage device each have icons that appear on the touchscreen in a format based on the user's preferences. Touching each of these icons will activate writing to each device. Alternatively, the user may only have one icon that is representative of multiple storage locations (e.g., local and remote hard drives) and a second icon for a removable drive such that the video stream is saved to the local and remote hard drives when selected but the removable drive is controlled separately. Still further, the system can be set up by the user as a preference to automatically save the entire video stream to selected storage devices but other storage locations only save the video stream when manually activated by the user.

The idea of soft configurability allows the user to pre-define or change/alter configurations to allow the user maximum freedom to control the system in a manner desired. If one user prefers a particular layout and control setup, this has no bearing on the next user who may have a completely different layout and control setup (e.g. they are left-handed as opposed to right-handed and prefer all controls opposite). It is understood that the configurable touchscreen could also be configured during a procedure if desired. For example, the user could touch an icon that allows for unlocking of the touchscreen such that icons may be moved as desired and then relocked into place. It is still further understood that questions could be presented to the user to make sure they intended to "unlock" the touchscreen or other screens prior to allowing the user to alter the current layout and control scheme.

The same is true with regard to the setup of control for the medical tools, medical equipment and operating room equipment. Icons representative of each may be provided on the touchscreen and be set to a setting that is predetermined according to the user's preferences. The icons can be positioned as desired and the "look" and "feel" of the icons themselves may be alterable if desired. For example, when a medical tool is in use, the icon may change to indicate the use. The icons may be changeable in numerous stages, for example, the icon for an irrigation pump may include a number superimposed over the icon to indicate the percentage of suction or may indicate a flow rate, and/or may change in color with the change in control. The goal of providing maximum configurability is to allow the user to configure the system to be as user friendly as possible to quickly and accurately provide information and control to the user to improve system operation and increase patient safety.

While a discussion has been presented with respect to the layout and control of the touchscreen, it should be understood that the entire system is configurable. For example, the data/information displayed on the main surgical monitor can be adjusted as desired in the same manner as discussed above in connection with the touchscreen with some, all or completely different information being displayed on the main surgical monitor as opposed to the touchscreen. Likewise, any number of monitors may be provided and configured as desired. For example, a monitor may be provided for the anesthesiologist that provides not only the vital signs of the patient, but also medical information relating to the patient's medical history or any other information desired. This monitor for the anesthesiologist could also comprise a touchscreen and allow the anesthesiologist to pull up information from the hospital information system (HIS) as desired, control the introduction of medication to the patient and provide feedback information on any of the other equipment in the system. It is understood that both the main touchscreen for the surgeon (user) and the secondary touchscreen for the anesthesiologist are independently soft configurable.

In still another embodiment, a redundant touchscreen can be provided at a "nurses station" that may be outside of the sterile environment but provide all the functionality of the primary touchscreen. In this manner, the user may be able to instruct a nurse or other personnel to make a particular adjustment or modify the system in a particular way while the surgeon is engaged in the surgical procedure.

In additional embodiments the system may include a "checklist" that is again configurable according to the user's preferences. The checklist may include certain procedures that are to be performed for a particular type of procedure. The checklist could be presented in the form of a question and answer that requires the user to indicate if a certain task was performed. The checklist could be presented as a statement that the settings of select devices have been present to indicated settings and requires an indication from the user that the setting is correct. The checklist could require the user to input information relating to the procedure or the patient prior to unlocking the system. It should be understood that virtually any procedure can be implemented based on the user's predefined preferences for a particular type of procedure. Additionally, the checklist could be configured as desired such that the user may add to the checklist even during the procedure.

As liability issues become an even greater concern for hospitals, it could be that a mandatory checklist is provided for a particular type of procedure such that the checklist is not allowed to be changed except by certain personnel. Alternatively, other types of protection for the hospital may be implemented to reduce potential liability, such that the system could require the user (surgeon) to blow into a breathalyzer to measure potential alcohol level prior to unlocking the system before a procedure.

Accordingly, centralized control of the entire operating room to manage endoscopic and peripheral devices and to view, display, document, and communicate information from video and other data sources both in and out of the operating room is provided.

Also provided are features (configurable icons) for easily connecting to audio-visual communication from the operating room, whether for teleconferencing, resident teaching or telesurgery and to network with hospital system like PACS, HIS, or RIS.

Still further, the ability to capture, display, annotate, save and route still images and video clips is provided. It is understood that the system could provide for user review prior to routing and/or saving of the still image or video clip. If, for example, the still image is not of the quality desired, the user could delete the still and capture another for review.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

In one embodiment of the present invention, an operating room control system comprising a computer having a network connection, an operating room system interface coupled to the computer, and a storage accessible by the computer. The system further comprises an endoscope generating a video output, the endoscope coupled to the operating room system interface, at least one medical tool coupled to the operating room system interface, and at least one piece of medical equipment coupled to the operating room system interface. The system still further comprises a touchscreen coupled to the operating room system interface, and a surgical monitor coupled to the operating room system interface. The system is provided such that software executes on the computer to present icons on the touchscreen associated with: the endoscope, the storage, the at least one medical tool, and the at least one piece of medical equipment, such that the icons allow for control of the devices and equipment associated therewith. The system is also provided such that the video output is displayed on the touchscreen and the surgical monitor, and the operating room control system is soft configurable such that the icons and the video output are configured and presented on the touchscreen based upon a user's defined configuration.

In another embodiment of the present invention, an operating room control system comprising a computer having a network connection, an operating room system interface coupled to the computer, and a plurality of storage devices accessible by the computer. The system further comprises an endoscope generating a video output, the endoscope coupled to the operating room system interface, at least one medical tool coupled to the operating room system interface, and a plurality of medical equipment coupled to the operating room system interface. The system still further comprises a touchscreen coupled to the operating room system interface, and a surgical monitor coupled to the operating room system interface. The system is provided such that software executes on the computer to present icons on the touchscreen associated with: the endoscope, the plurality of storage devices, and the plurality of medical equipment, such that the icons allow for control of the devices and equipment associated therewith. The system is also provided such that the video output is displayed on the touchscreen and the surgical monitor, and the operating room control system is soft configurable such that the icons and the video output are configured and presented on the touchscreen and the surgical monitor based upon a user's defined configuration.

Other objects of the invention and its particular features and advantages will become more apparent from consideration of the following drawings and accompanying detailed description.

DETAILED DESCRIPTION OF THE INVENTION

Figure 1:
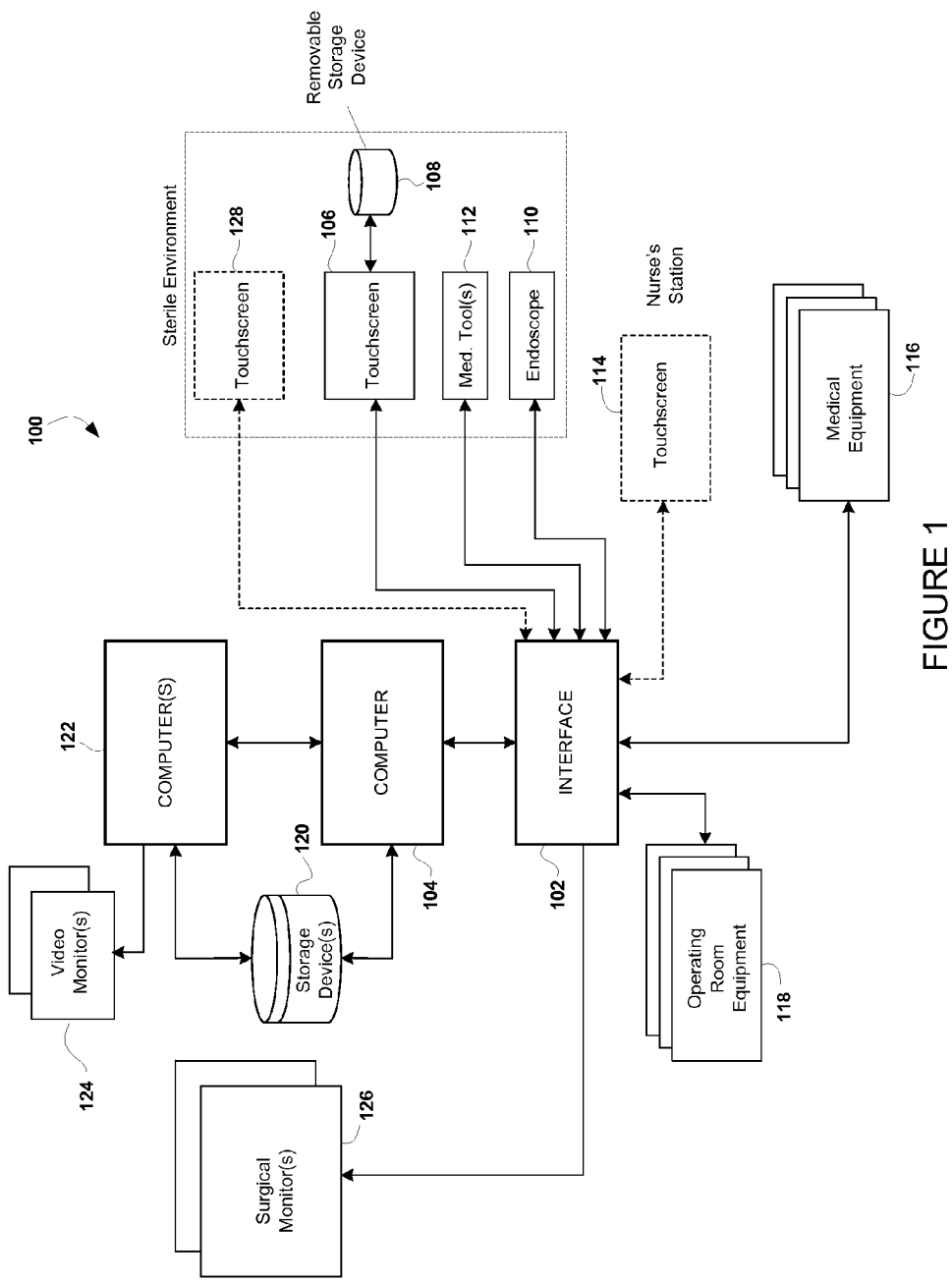
FIG. 1 is a block diagram of an embodiment of the present invention.

Referring now to the drawings, wherein like reference numerals designate corresponding structure throughout the views.

FIG. 1 is a block diagram illustrating an advantageous embodiment of operating room control system 100. In this embodiment, operating room control system 100 is shown including Interface 102, which is coupled to computer 104. The interface 102 would typically be positioned or located in the operating room in proximity to the various equipment connected thereto and in one embodiment would be rack-mounted. It is further understood that computer 104 may also be located in the operating room and rack-mounted, however, this is not required as the interface 102 could be coupled to computer 104 via a network connection.

Connected to interface 102 is touchscreen 106, which provides an interface for the user to control and interface with operating room control system 100. Touchscreen 106 is shown positioned in the sterile environment and is accessible by, for example, a surgeon performing a procedure. The touchscreen 106 may comprise virtually any type of commercially available touchscreen device and would typically be mounted on a boom or arm allowing the user to position the touchscreen 106 in a manner convenient for use (e.g., adjacent to or over the patient). Also illustrated in FIG. 1 is removable storage device 108 shown coupled to touchscreen 106. Removable storage device 108 may comprise virtually any type of data storage device that may be detachably connected to operating room control system 100. In one advantageous embodiment, removable storage device 108 comprises a thumb drive (e.g., a USB storage device). While removable storage device 108 is illustrated connected to touchscreen 106, it is understood that it may be connected to operating room control system 100 at numerous different locations including, for example, interface 102, computer 104 or any of the other touchscreens.

Also illustrated in FIG. 1 is endoscope 110 and medical tool(s) 112 connected to interface 102. Endoscope 110 may comprise virtually any type of video endoscope that allows for visualization of a surgical site inside of the body and may be flexible or rigid and have a detachable or integral camera. It is further contemplated that endoscope 110 may utilize a wired or wireless connection to interface 102 and have a CCD or CMOS imager (not shown) positioned on the endoscope for converting received light to a digital image stream.

Likewise, medical tool(s) 112 may comprise a wide variety of medical tools used by the surgeon including, but not limited to: catheterization devices, bi-polar cutting devices, lasers, rotating cutting devices, cell collection devices, suction devices and the like. It is understood that many of these medical tools 112 may be manufactured by different companies and therefore the command and control signals for each of the medical tools may differ. Interface 102 is provided to interface between the numerous differing types of signal formats such that the user may control a medical tool(s) from the touchscreen 106 if desired. Additionally, the user has the option to control the endoscope 110 from the touchscreen 106 if desired. It should be noted that many, if not all of the medical tools 112 and endoscope 110 have controls positioned directly thereon such that the surgeon may control the medical tool(s) 112 and endoscope 110 by manipulating the control interface on the device itself as opposed to the touchscreen 106.

Also illustrated in FIG. 1 is a second touchscreen 114, which is provided with a notation (nurse's station) indicating that this second touchscreen 114 may be located at the nurse's station. The broken line indicates that this second touchscreen is an optional feature. It is contemplated that second touchscreen 114 may be redundant to and provide all the functionality of touchscreen 106 but is positioned outside of the sterile environment. In this manner, a nurse has the ability to make an adjustment based on the surgeon's direction if, for example, it is not convenient for the surgeon to do so on touchscreen 106. It is also contemplated that additional features or a different configuration may be provided for touchscreen 114 as opposed to touchscreen 106. For example, touchscreen 106 may provide a video feed from endoscope 110 in addition to various interfaces allowing control of endoscope 110 and medical tool(s) 112, however, it may not be necessary to provide the video feed to touchscreen 114. The system is completely configurable allowing the touchscreens (106, 114) to be configured in a manner desired. It is further understood that touchscreen 114 may be mounted on a boom or an arm and be positioned in proximity to a rack holding medical equipment 116.

Medical equipment 116 is illustrated having a number of boxes to indicate that there may be a plurality of medical equipment 116 connected to interface 102. Typically medical equipment 116 will be rack-mounted on a rack with wheels allowing for the equipment to be placed conveniently and in proximity to the sterile environment. Medical equipment 116 will vary depending on the procedure being performed, however, to provide some context to the types of equipment that medical equipment 116 may comprise, a non-exhaustive list is provided including: insufflations equipment, irrigation equipment, vacuum equipment and the like. It should be understood that a great number of different types of equipment may be used depending upon the procedure to be performed. Like the medical tool(s) 112, it is contemplated that medical equipment 116 will be equipment manufactured by many different companies and therefore have command and control signals with diverse formats and requirements. Accordingly, interface 102 is provided to send and receive data to and from the various medical equipment 116 such that the medical equipment 116 may be controlled from either touchscreen 106 or touchscreen 114. It is further understood that the various medical equipment 116 may be directly controlled by interfaces on the front panels of medical equipment 116 by, for example, a nurse at the nurse's station under direction of the surgeon.

Also shown in FIG. 1 is operating room equipment 118 connected to interface 102. Like medical equipment 116, operating room equipment 118 is controllable from either touchscreen 106 or touchscreen 114. Operating room equipment 118 may comprise a wide variety of equipment that may be desirable to control by the surgeon or nurse including, but not limited to, the operating room lights, the operating room blinds or shades, and the positioning of the operating room table. Operating room equipment 118 may also comprise hospital system including PACS, HIS and RIS, and remote image storage systems. For example, it may be advantageous for the surgeon (or nurse) to access the patient's medical records to verify treatment, conditions or status prior to or during the procedure. Likewise, the surgeon may desire to access a medical image (e.g., an MRI or x-ray) of the patient before or during a procedure. All of these options are available to the user via the touchscreen.

Still further, storage device(s) 120 is shown connected to computer 104 and/or computer(s) 122. Storage device(s) 120 may comprise virtually any type of digital storage device including, solid state hard drive devices, magnetic hard drives devices, optical drive devices, removable storage devices and the like. For example, it may be desired to record a part or all of the procedure from the video endoscope 110 to a DVD inserted into computer 104. However, it may further be desired to save a part or all of the procedure to a hard drive device in the hospital information system for the hospitals records. Still further, the surgeon may desire to save a part or all of the procedure directly to a storage device on the surgeon's computer in the surgeon's office. There are many differing configurations that may be specified by the user either before or even during the procedure allowing for maximum system flexibility.

Video monitor(s) 124 is also illustrated connected to computer(s) 122. It should be understood that operating room control system 100 allows for video feeds to remote locations for telesurgery and teleconferencing such that a surgeon at a remote location could view the surgical procedure and provide input or comments to the surgeon performing the procedure. In addition, a video feed could be provided to a classroom environment for educational purposes so that medical students have the opportunity to see a particular medical procedure from a remote location.

Surgical monitor(s) 126 are shown connected to interface 102 and may comprise one or more surgical monitors positioned in the operating room. Typically a main surgical monitor (typically a large (40"-60") flat panel display) is provided in the operating room and quite often numerous surgical monitors are positioned at various locations in the operating room. It is contemplated that the video feed from the video endoscope 110 will be displayed on surgical monitor(s) 126, however, the touchscreens allow the user to display virtually any information thereon as desired. While surgical monitor(s) 126 are shown connected to interface 102, it is understood that they may alternatively be directly connected to computer 104.

A third touchscreen 128 is also illustrated positioned in or adjacent to the sterile environment and connected to interface 102. Again, this touchscreen is shown in dashed line to indicate that it is optional. Touchscreen 128 may be provided for an anesthesiologist to view the patient's vital signs and control the administration of anesthesia to the patient. It is understood that touchscreen 128 may provide control of various medical equipment 116 as previously discussed, and may have the ability to access, for example, the hospital information system to pull up the patient's records and information. Still further, the anesthesiologist may be provided with the ability to record or save the information presented on touchscreen 128 as desired in a manner and to any of the storage devices previously discussed. The idea is to provide maximum flexibility to the system users to increase safety, efficiency and ease of use.

Figure 2:
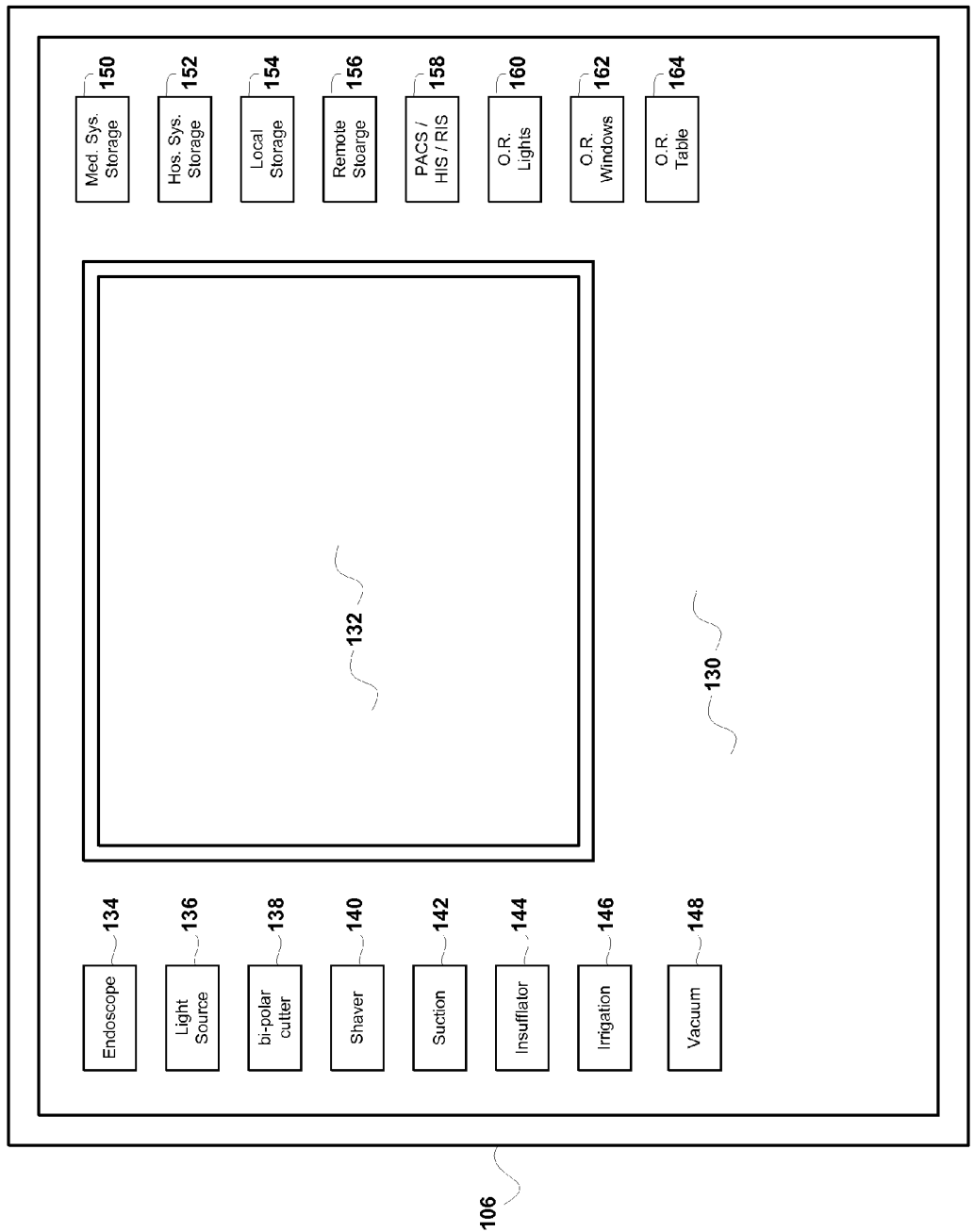
FIG. 2 is an illustration of the touchscreen according to the embodiment of FIG. 1.

Turning now to FIG. 2, a view of touchscreen 106 is provided. While touchscreen 106 is discussed in connection with the following FIGS, it should be understood that any or all of the description may be applicable to touchscreens 114 and 128.

Touchscreen 106 is provided with a front panel 130 on which various data are displayed to the user. For example, in the top center of front panel 130, video display 132 is positioned. Video display 132 will provide the video feed from endoscope 110 such that the user will be able to see a live video feed on the touchscreen 106.

Also shown on front panel 130 are various icons associated with various devices including: endoscope icon 134, light source icon 136, bi-polar cutter icon 138, shaver icon 140, suction icon 142, insufflators icon 144, irrigation icon 146 and vacuum icon 148. These icons are associated with various medical tools and medical equipment. It should be understood that some, all or different icons may be presented on front panel 130 depending on the medical procedure to be performed and those indicated are only provided to indicate some of the types of devices/equipment that may be connected thereto and used by the surgeon.

On the right side of front panel 130 additional icons are illustrated including: medical system storage 150, hospital system storage 152, local storage 154, remote storage 156, PAC/HIS/RIS 158, operating room lights 160, operating room windows 162 and operating room table 164. Again, it should be understood that while certain types of hospital/medical storage devices and locations/systems and certain types of operating room equipment are listed here, this is not meant to be an exhaustive list as those of skill in the art would understand that many differing types of systems may advantageously be connected to and brought under the control of the operating room control system 100 without deviating from the invention disclosed herein. The system 100 is soft configurable meaning that the system is completely configurable based on the user's preferences. Accordingly, the surgeon may have particular tools/equipment that he/she prefers to use for a particular procedure. The layout of the tools/equipment icons on the touchscreen 106 may be completely configured, as well as the settings for each tool/equipment.

Figure 3:
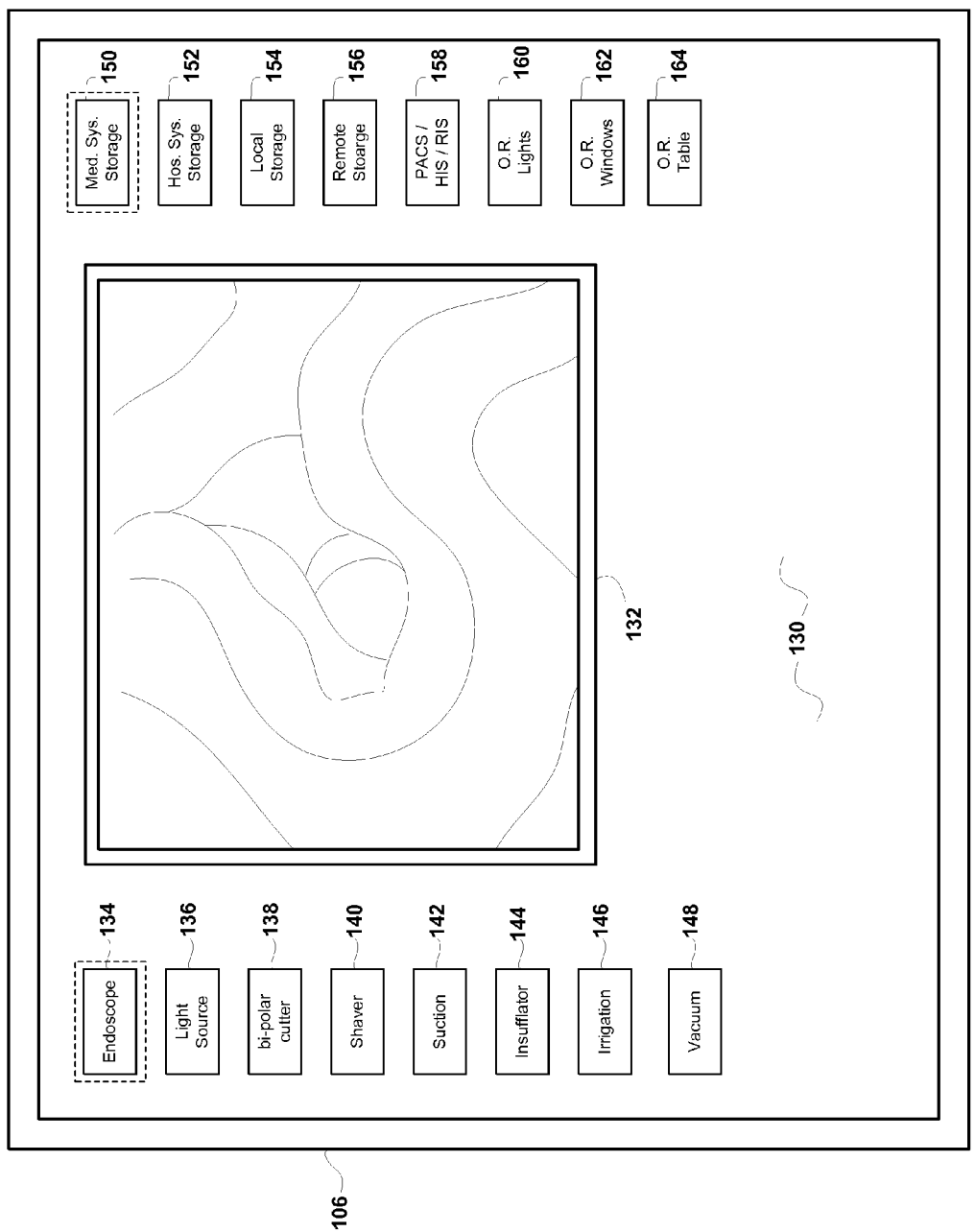
FIG. 3 is an illustration of the touchscreen according to the embodiment of FIG. 2.

Referring now to FIG. 3, touchscreen 106 is illustrated with endoscope icon 134 highlighted indicating that the user has activated endoscope icon 134 by touching the appropriate location on the front panel 130 of touchscreen 106. As video endoscope 110 is associated with endoscope icon 134, a video stream of images is now shown in video display 132 corresponding to a video output endoscope 110. It is understood that endoscope icon 134, while shown as a box labeled "endoscope" may be provided as a picture or image representative of the endoscope. Likewise, while a dashed line is illustrated surrounding the box labeled "endoscope" it is understood that numerous ways of highlighting endoscope icon 134 may be utilized, including, for example, changing a color of the icon to "green" indicating that the device is operating.

Also illustrated in FIG. 3 is medical system storage icon 150, which again may be provided as any type picture or image representative of the storage. The highlighting (again may be a change in color as previously discussed) can indicate that recording (saving) of the video image stream presented in video display 132 is occurring. The saving of the video stream to a storage device associated with medical system storage icon 150 may initiate when the user touches the icon or may occur automatically when the video stream is transmitted to video display 132. This is completely configurable according to the user's preferences.

Figure 4:
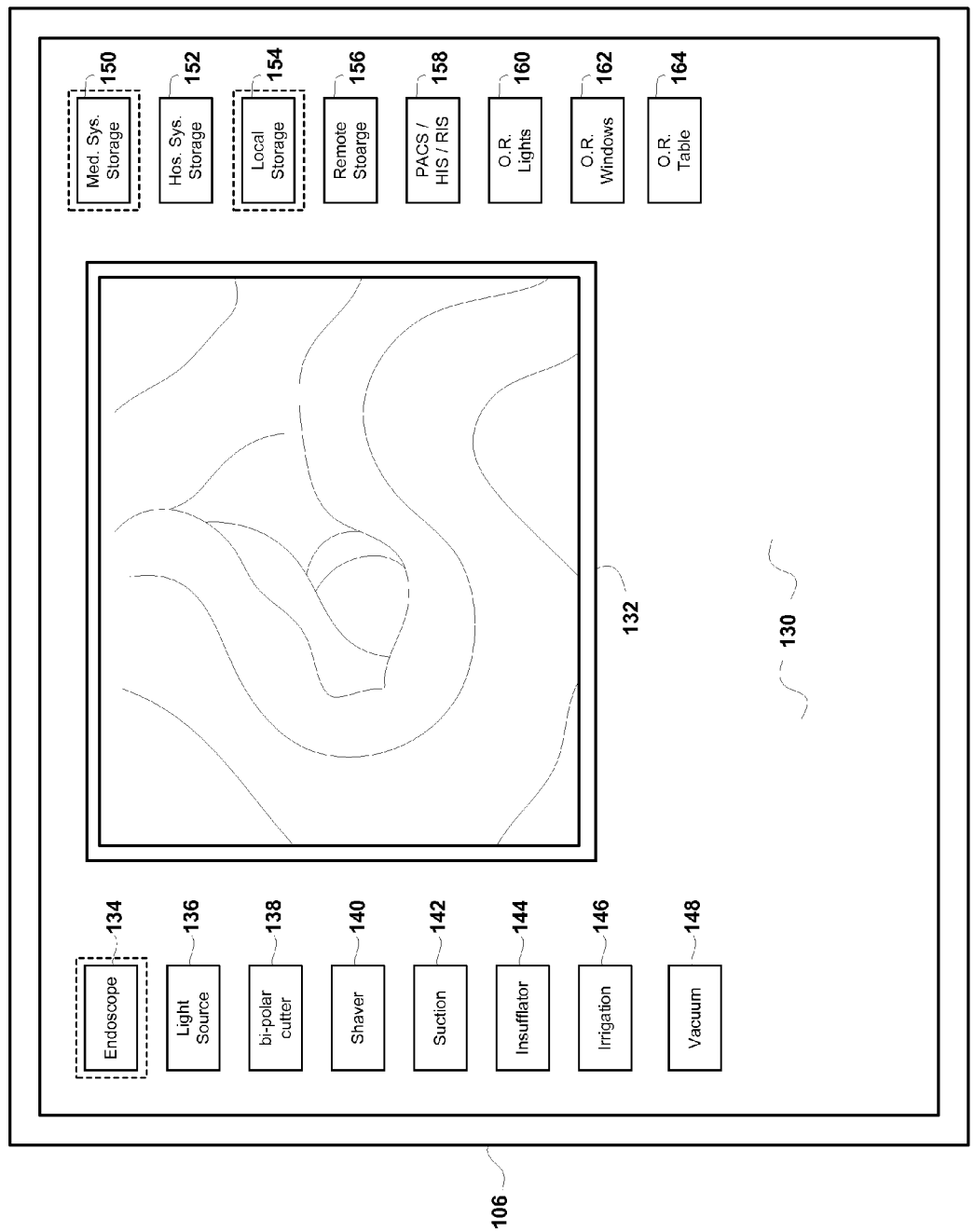
FIG. 4 is an illustration of the touchscreen according to the embodiment of FIG. 2.

FIG. 4 illustrates highlighting around local storage icon 154. This figure indicates that the user (surgeon/nurse) may desire to have a portion of the video stream recorded or saved to a local or removable storage device. The user then, only has to touch the local storage icon 154, which can change (e.g., color) to indicate to the user that the video stream is recording to the local storage device. When the portion of the video stream is recorded as desired, the user only need touch the local storage icon a second time to interrupt recording, which can again be indicated by a change in the icon (e.g., change color to "red") to provide a visible indication that recording has stopped. Recording may be resumed by simply touching the icon again. In this manner, the recording system is very simple and easy to use. It should also be noted that multiple storage devices may be associated with a single icon such that the video stream may be written to, for example, a DVD in the operating room and to a hard drive accessible by the hospital information system. Any combination of storage devices may be written to automatically or manually as desired and defined by the user's predefined preferences.

Figure 5:
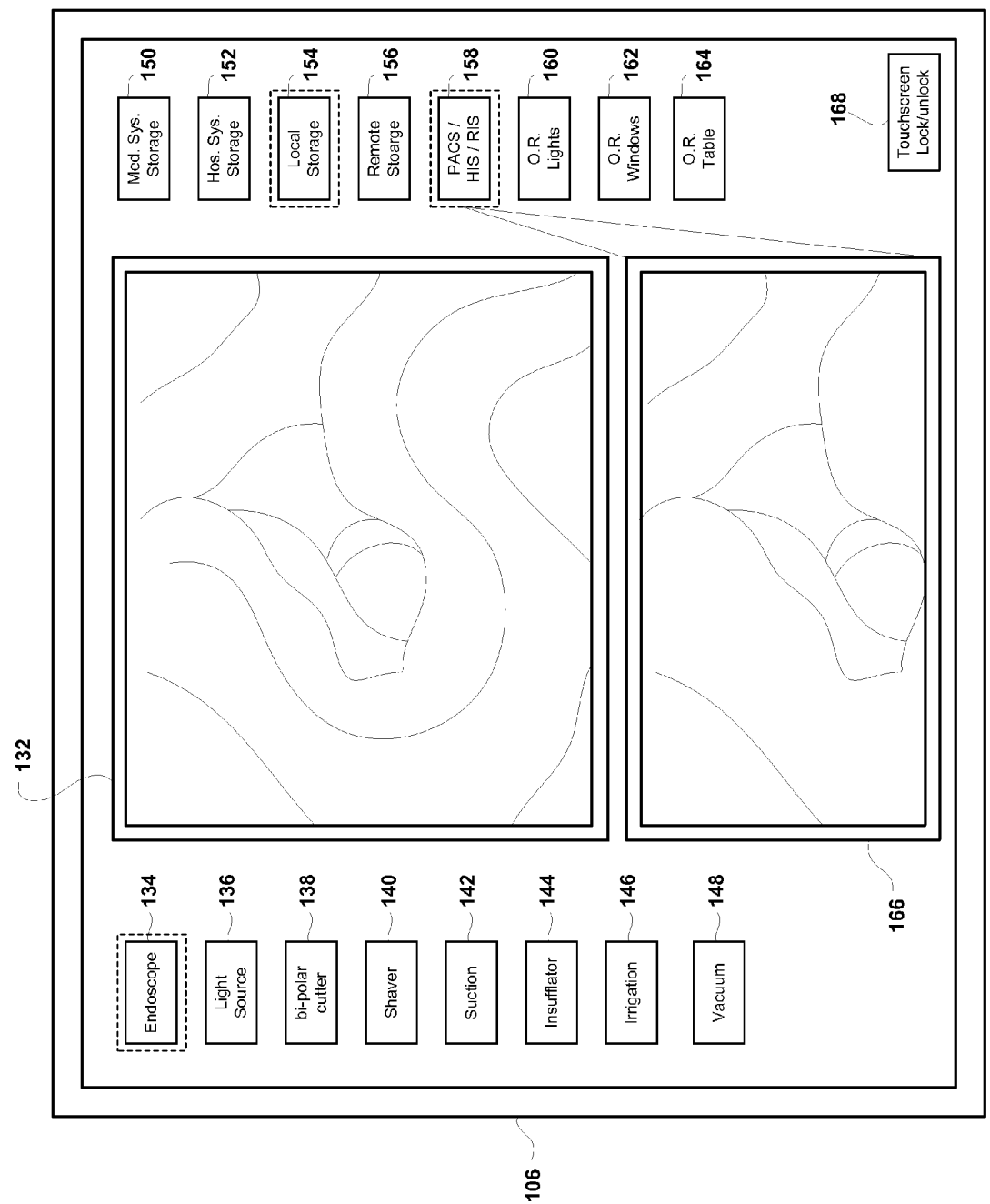
FIG. 5 is an illustration of the touchscreen according to the embodiment of FIG. 2.

FIG. 5 illustrates another view of touchscreen 106 in which PACS/HIS/RIS icon 158 has been activated and an image display 166 is provided below video display 132. In this embodiment, the operating room control system 100 allows the user to access a medical image that is accessed through, for example, the hospital information system. In this way, the surgeon can look up prior images of the area, or view an MRI or an x-ray, etc. While a medical image is shown in FIG. 5, it should be understood that any information relating to the patient may be viewed including, for example, the patient's medical history or any other information that may be accessed through PACS/HIS/RIS.

Figure 6:
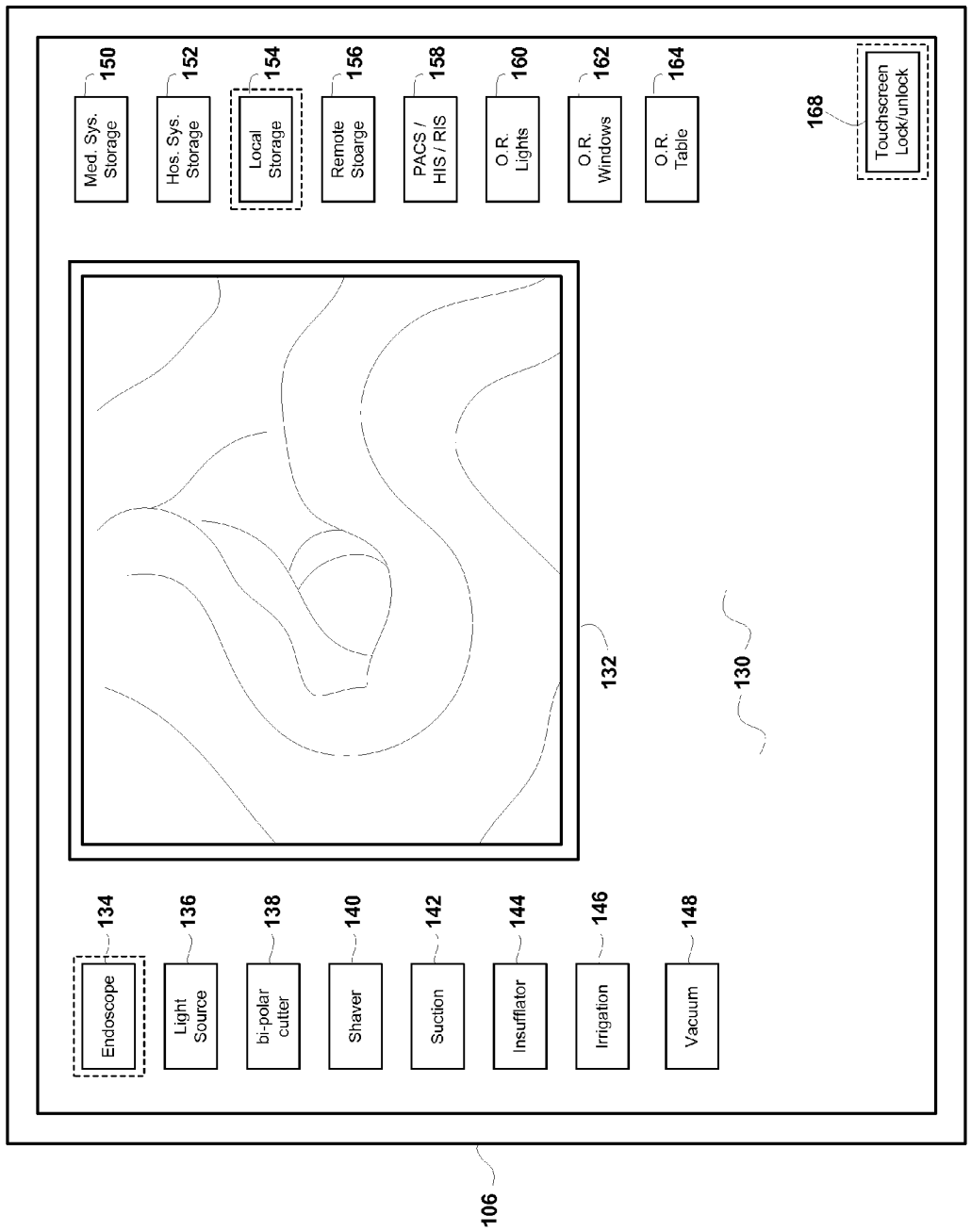
FIG. 6 is an illustration of the touchscreen according to the embodiment of FIG. 2.

Also shown in FIG. 5 at the bottom right-hand side of front panel 130 is touchscreen lock/unlock icon 168. As illustrated in FIG. 6, the touchscreen lock/unlock icon 168 may be activated so as to allow the touchscreen 106 to toggle between a locked state and an unlocked state. In the locked state, the various information displayed on front panel 130 is "locked" in the positioning shown. However, the user has the ability to "unlock" the touchscreen 106 to allow for complete configuration of the positioning of the information as shown in FIG. 7.

Figure 7:
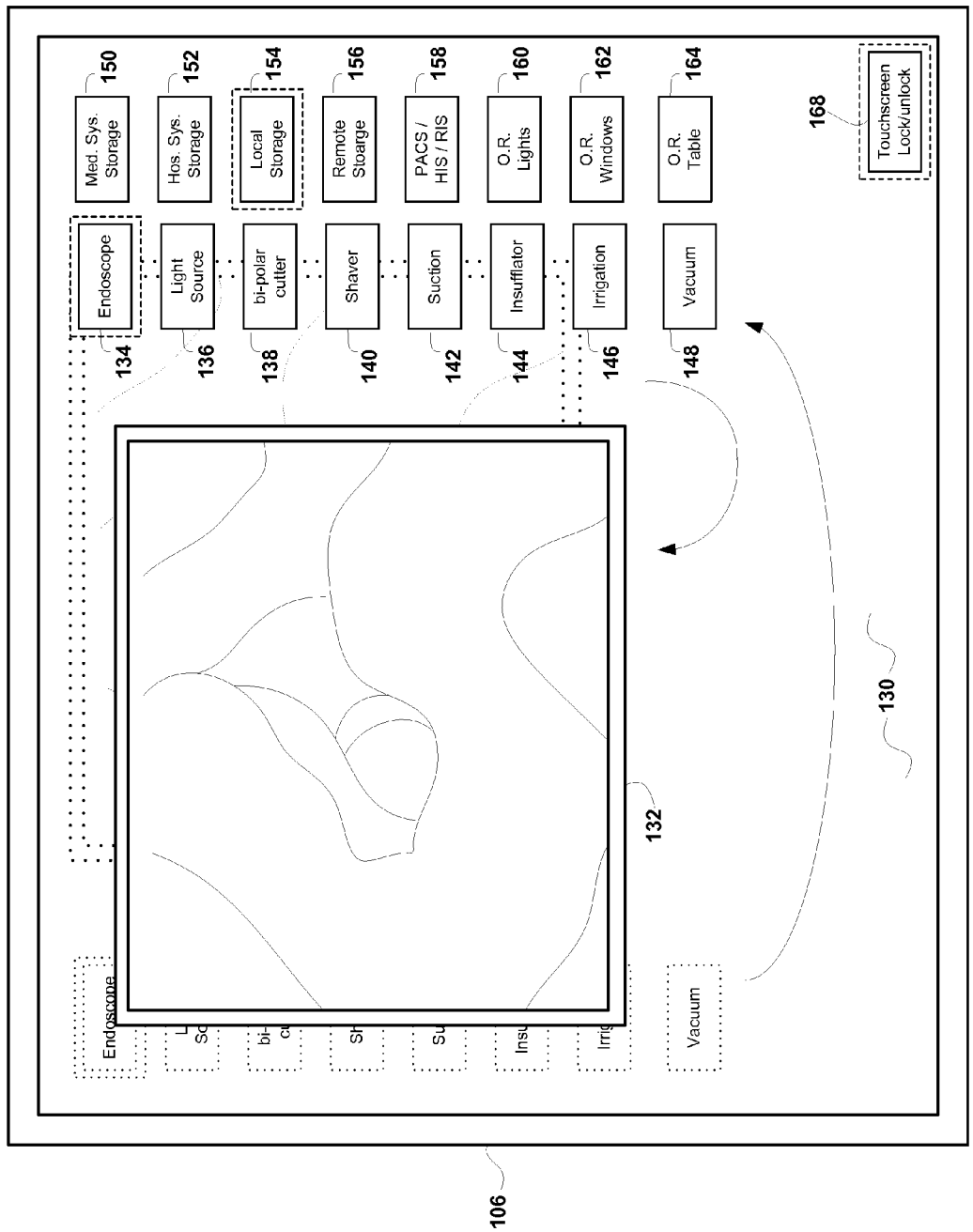
FIG. 7 is an illustration of the touchscreen according to the embodiment of FIG. 2.

As can be seen in FIG. 7, by unlocking the touchscreen 106, the user has the ability to move or reposition the various data being displayed on front panel 130 (e.g., the system 100 is "soft configurable"). The user need only touch the item they want to move and drag it to the new location on the front panel 130. This allows the user maximum configurability for the system. For example, while the example presented in FIG. 7 shows the movement of the video display 132 and the icons on the left side of the front panel 130 being moved, the user could group icons, move icons, move the video display 132, overlay or do virtually anything with the data displayed on the front panel 130 to configure the touchscreen 106 in a manner that is most desirable for the particular user. It is contemplated that all of this configurability could further be accomplished prior to the procedure such that the entire system is preconfigured in accordance with the particular surgeon's configuration requirements simply by identification of the surgeon.

Figure 8:
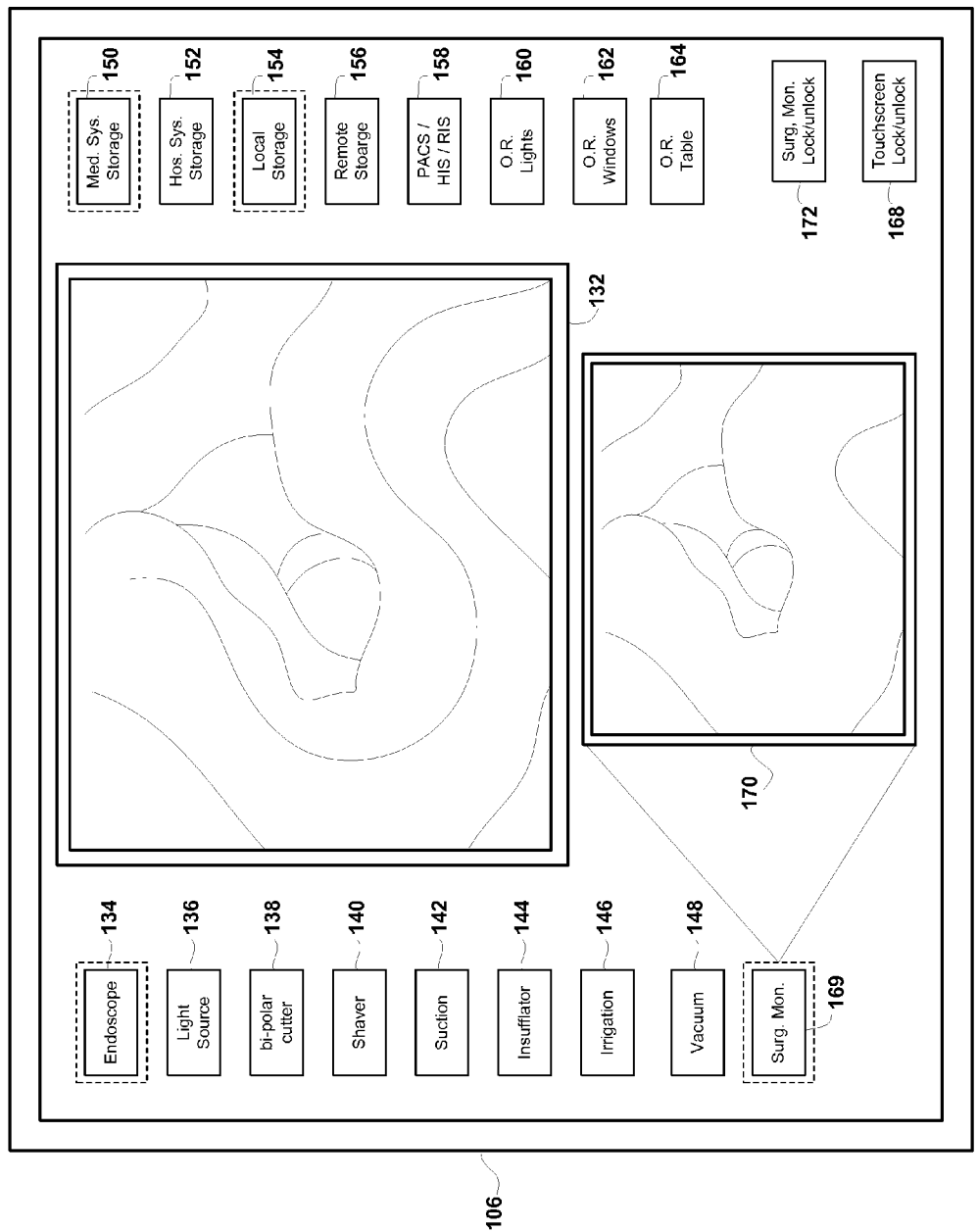
FIG. 8 is an illustration of the touchscreen according to the embodiment of FIG. 2.
Figure 9:
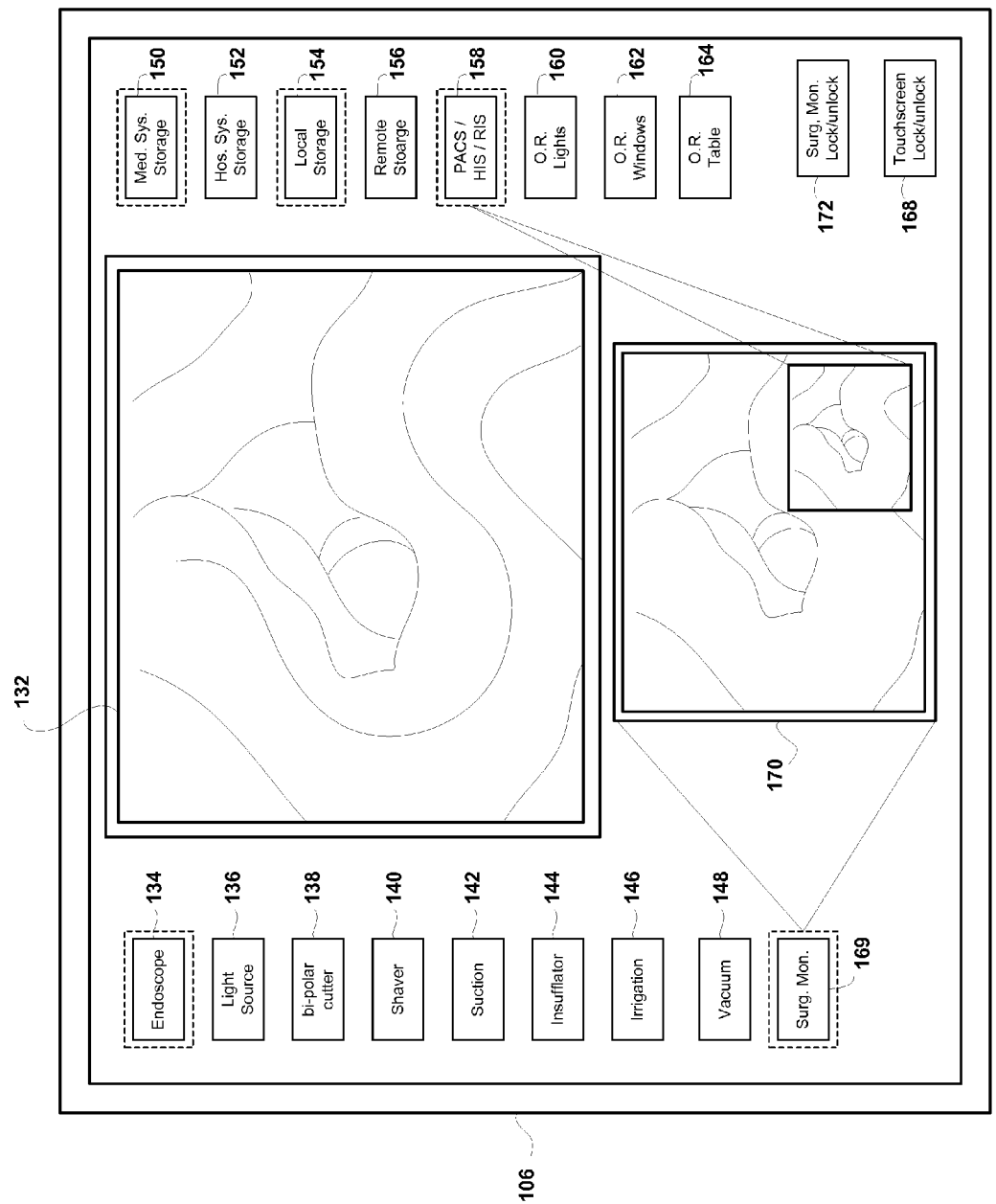
FIG. 9 is an illustration of the touchscreen according to the embodiment of FIG. 2.
Figure 10:
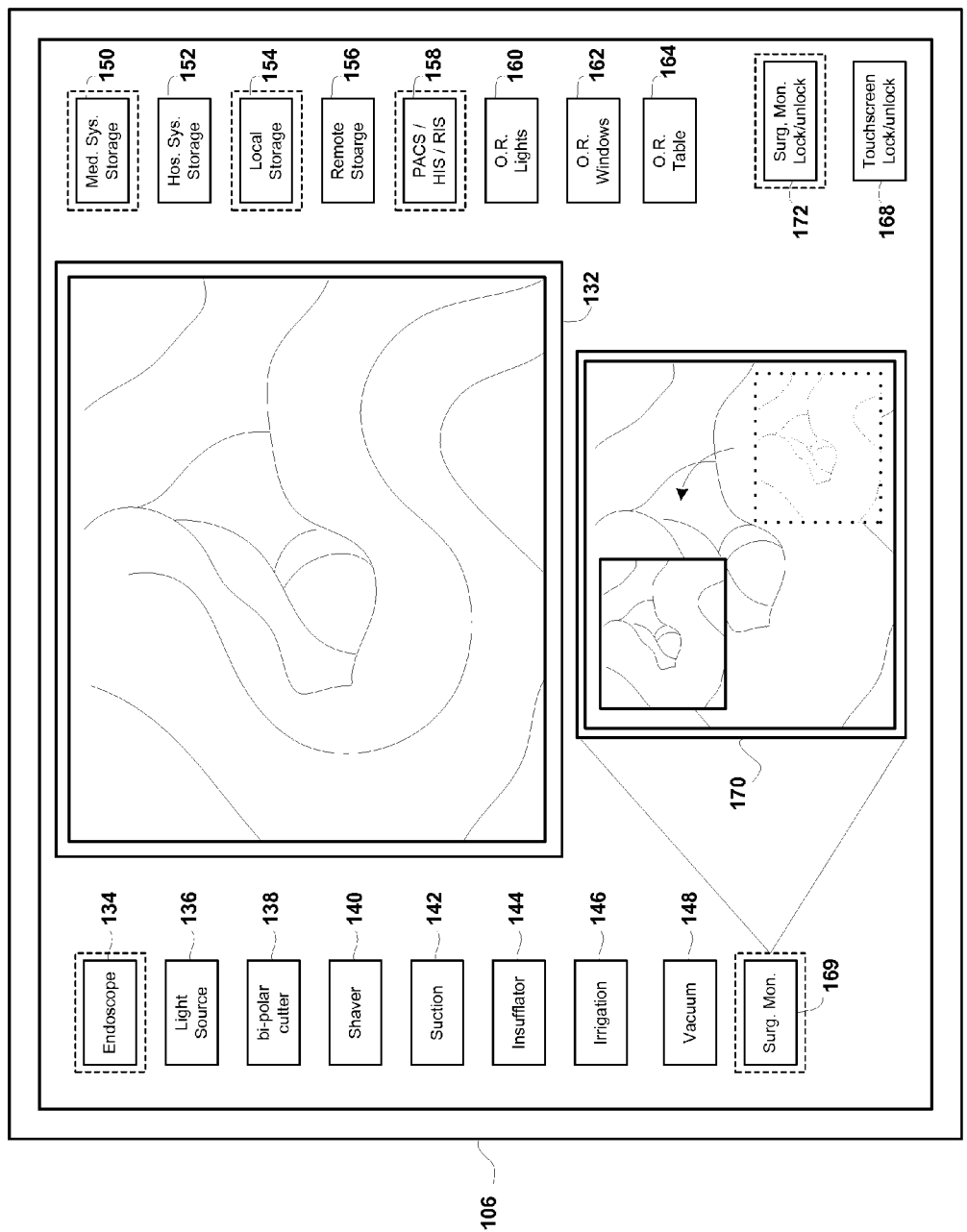
FIG. 10 is an illustration of the touchscreen according to the embodiment of FIG. 2.

Referring now to FIGS. 8-10, another embodiment of the present invention is illustrated relating to the surgical monitor 126. In FIG. 8 a surgical monitor icon 169 is activated bringing up a surgical monitor display 170 on front panel 130. The surgical monitor display 170 shows the information that is currently being displayed on surgical monitor 126.

FIG. 9 shows the activation of PACS/HIS/RIS icon 158, which brings up a medical image that is overlaid in the surgical monitor display 170 and simultaneously displayed on surgical monitor 126 in the same manner as shown in surgical monitor display 170. This allows for medical images/information to be displayed on the surgical monitor 126 such that it may be viewed by other surgeons that may be in the operating room. Alternatively, the medical image could be overlaid and sent to video monitor 124 for viewing by another surgeon remotely located from the operating room for telesurgery or to a classroom setting (e.g., showing an x-ray of a broken bone prior to the orthopedic surgical procedure, etc.).

FIG. 10 shows still another icon labeled surgical monitor lock/unlock icon 172 that has been activated. This embodiment is similar to that described in connection with FIG. 7, however, in this case the user has the ability to move the medical image around in the surgical monitor display 170, which in turn, repositioned the medical image on surgical monitor 126.

Figure 11:
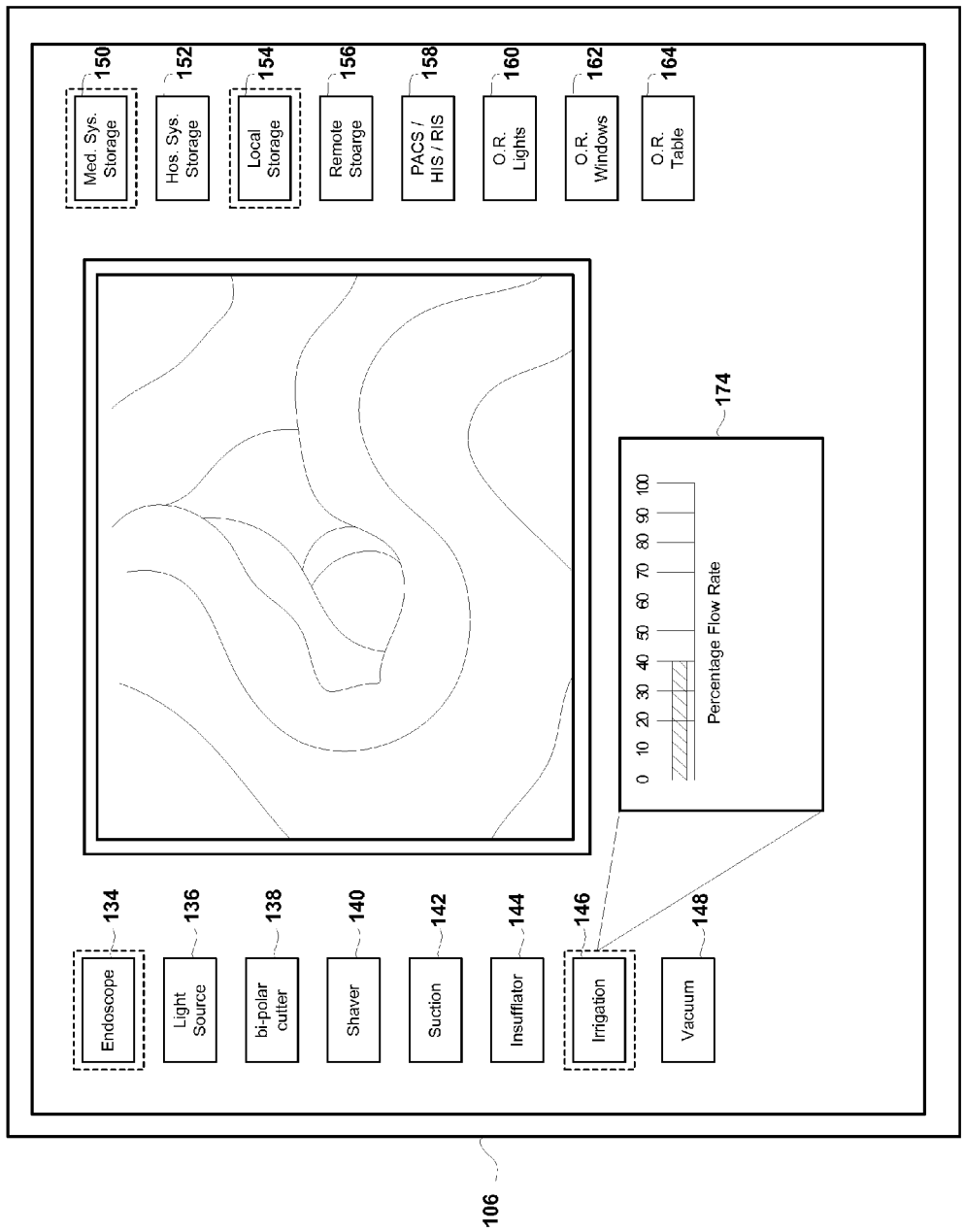
FIG. 11 is an illustration of the touchscreen according to the embodiment of FIG. 2.
Figure 12:
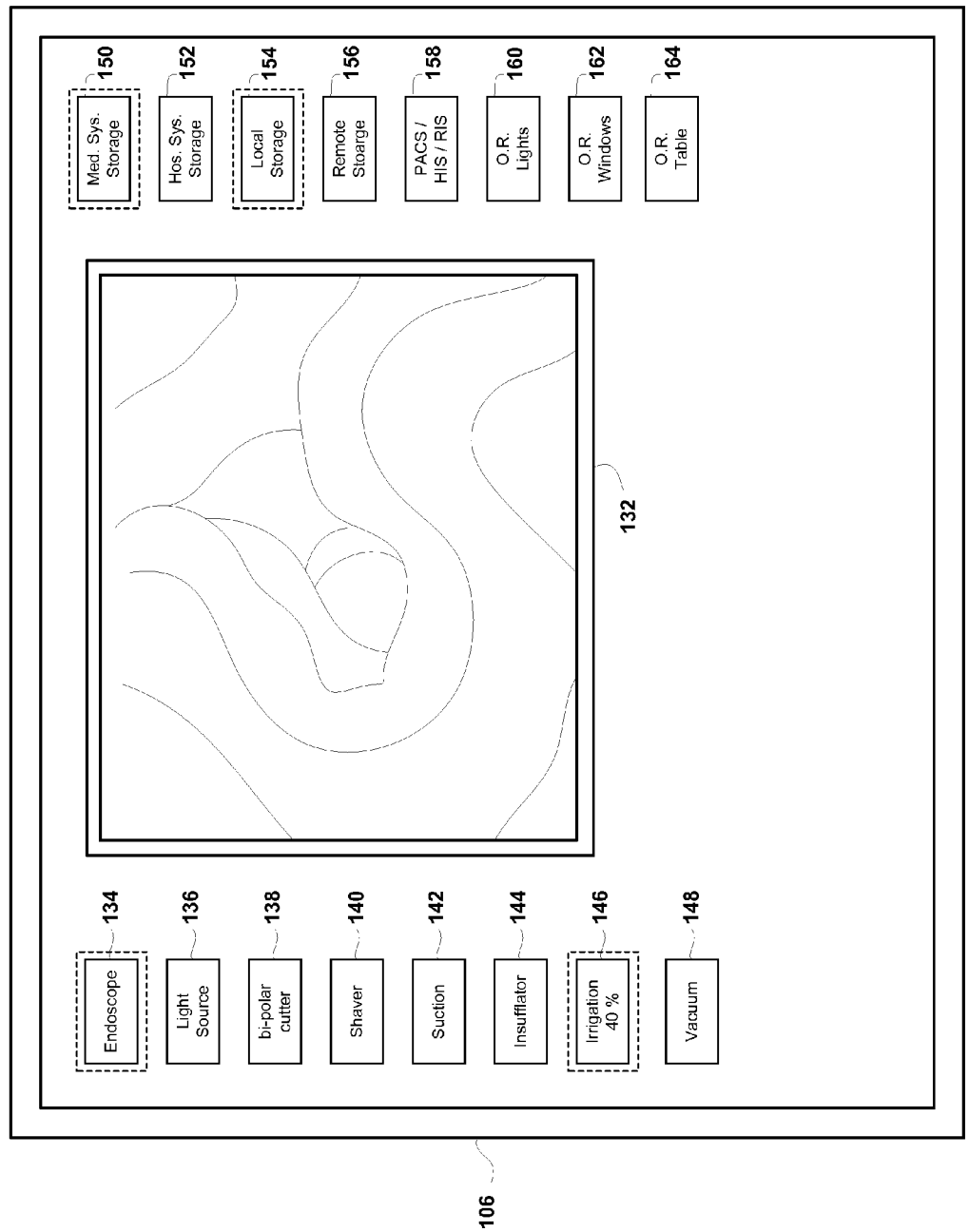
FIG. 12 is an illustration of the touchscreen according to the embodiment of FIG. 2.

Turning now to FIGS. 11 and 12, the irrigation icon 146 has been activated. It should be understood that activation of the icons can result in a visible change to the icons to indicate that the device associated with the icon is active. In this case, an irrigation interface 174 is displayed on front panel 130 indicating a setting of the irrigation equipment. Here, the user need only touch the irrigation interface 174 at the location corresponding to the desired setting (in this case 40%) to set the device. FIG. 12 illustrates that the irrigation interface 174 has been removed as the irrigation device is now set (this could occur by touching the irrigation icon 146 a second time). However, a numerical value is now shown on the irrigation icon 146 (40%) such that information is conveyed to the user even without the irrigation interface 174 being shown. It is further understood that the color of the irrigation icon could change according to the setting from 0% up to 100%.

Figure 13:
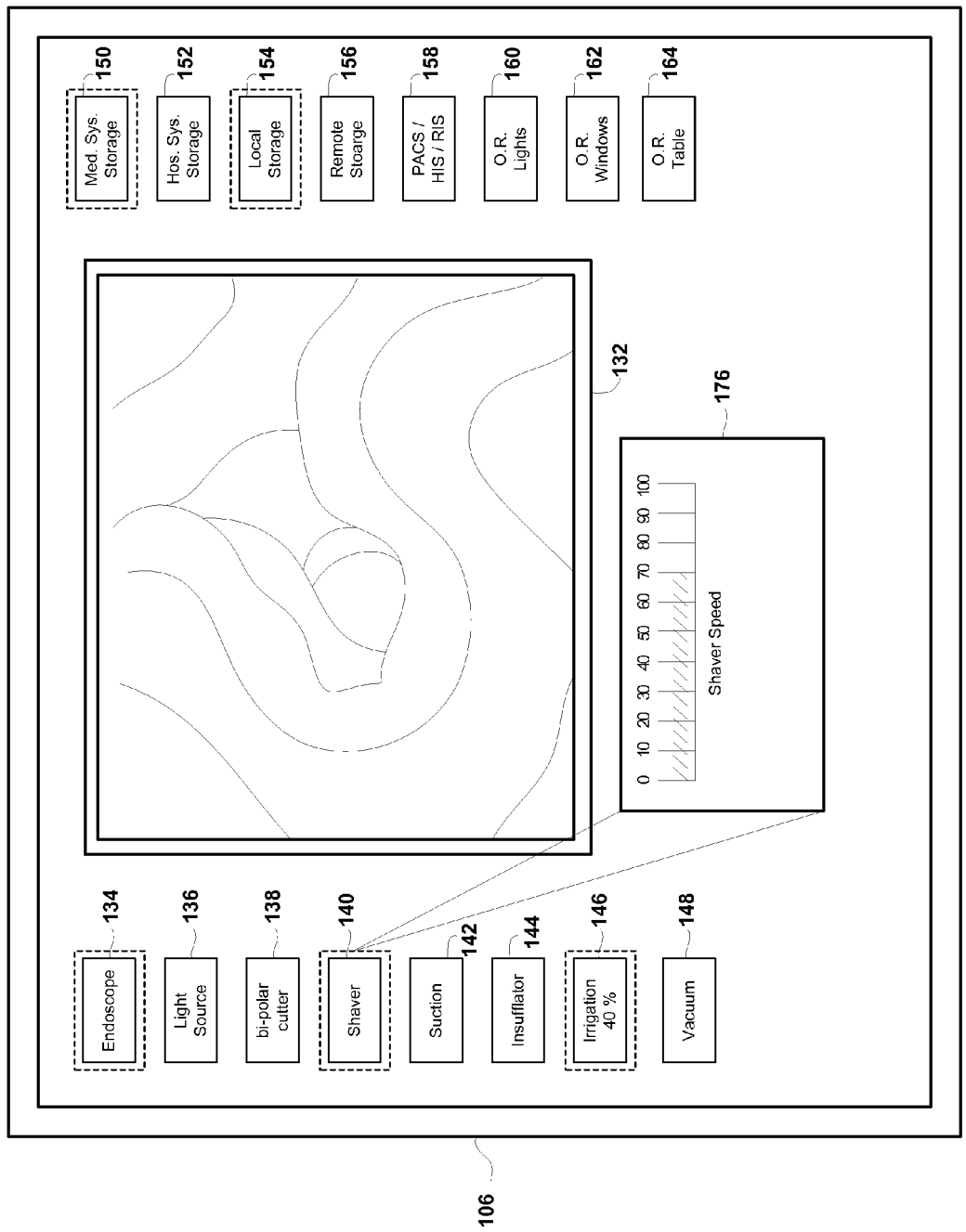
FIG. 13 is an illustration of the touchscreen according to the embodiment of FIG. 2.
Figure 14:
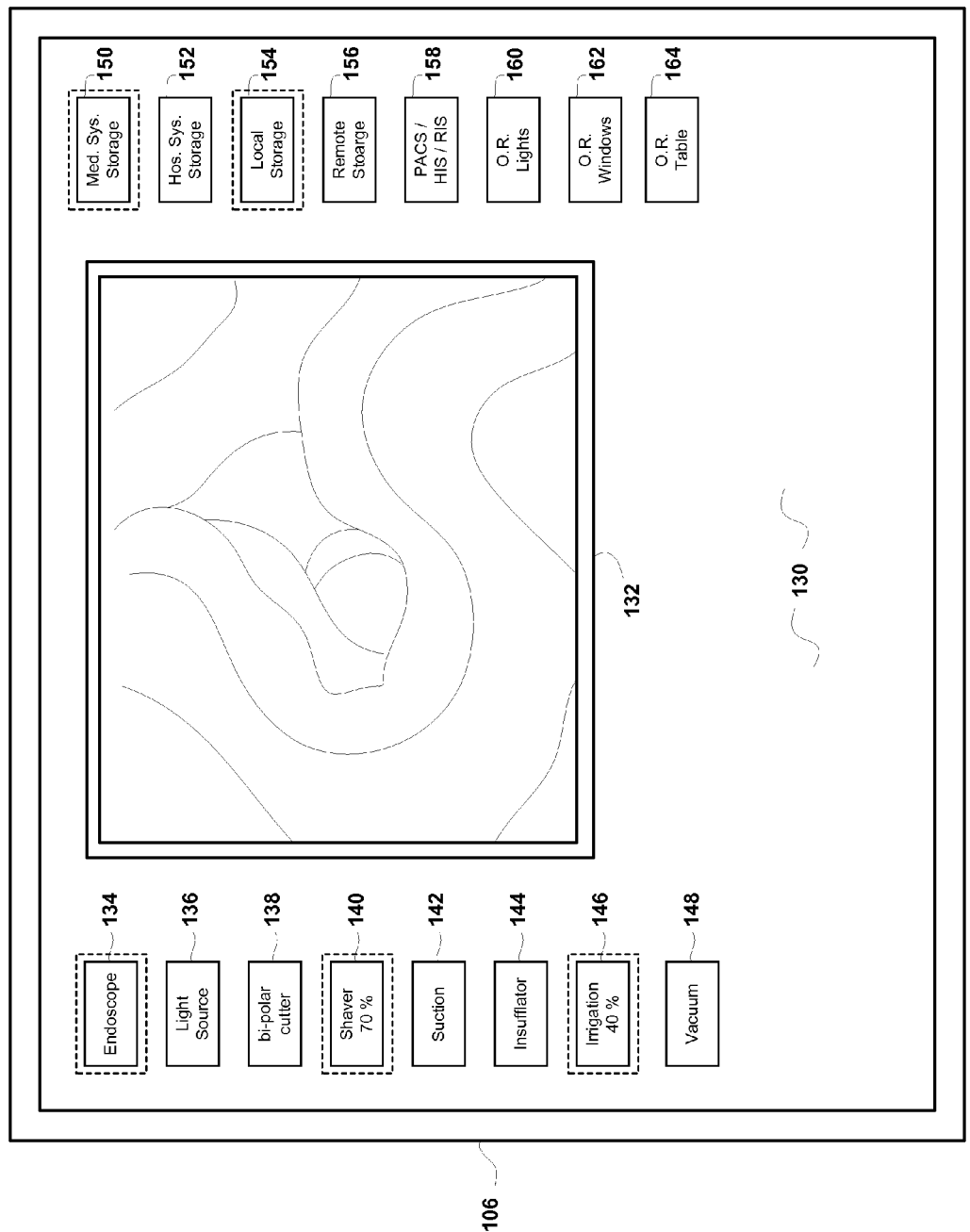
FIG. 14 is an illustration of the touchscreen according to the embodiment of FIG. 2.

FIGS. 13 and 14 illustrate additional functionality of the operating room control system 100. Here shaver icon 140 has been activated, which works to display shaver interface 176 on front panel 130 indicating a setting of the shaver. As discussed in connection with the irrigation equipment, the shaver may be set by the user to a particular setting as indicated. Additionally, once set, the shaver interface 176 can be removed and the shaver icon 140 can display the setting of the shaver (e.g. shaver speed 70%) as illustrated in FIG. 14.

Figure 15:
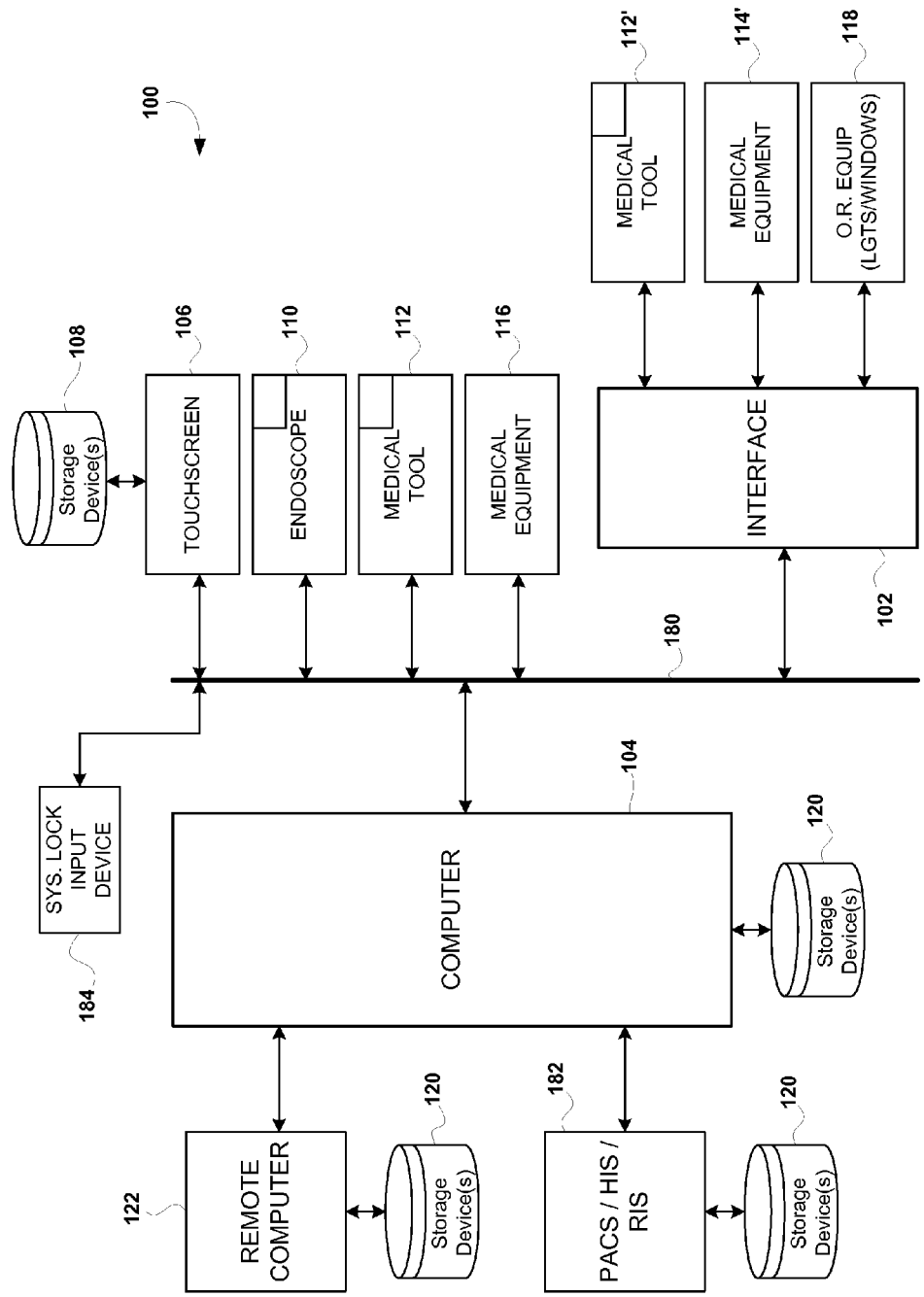
FIG. 15 is a block diagram according to the embodiment of FIG. 1.

FIG. 15 is a block diagram of operating room control system 100 according to the embodiment discussed in connection with FIG. 1. Many of the features are similar to those described in connection with FIG. 1 and will not be repeated here. However, additional functionality is provided in that touchscreen 106, endoscope 110, medical tool 112 and medical equipment 116 are connected to bus 180, which is in turn connected to computer 104 and interface 102. Additional equipment, medical tool 112', medical equipment 114' and operating room equipment 118 are connected to interface 102. In this embodiment, it is contemplated that the devices connected to interface 102 are manufactured by different companies and therefore comprise differing signal formats and levels. Whereas the devices coupled directly to the bus 180 may share a common signal format.

Also shown in FIG. 15 is PACS/HIS/RIS 182, which may comprise any system the hospital is using for management of their medical information. This system is accessible by computer 104 such that activation of the touchscreen in a manner previously described can function to save information to the hospital system or access information stored on the hospital system.

Still further provided is a system lock input device 184 that locks the entire operating room control system 100 until an input is received that is within a predetermined acceptable range. It is contemplated that this input can range from any of a wide range of data that the hospital may want to receive prior to unlocking the system 100.

Figure 16:
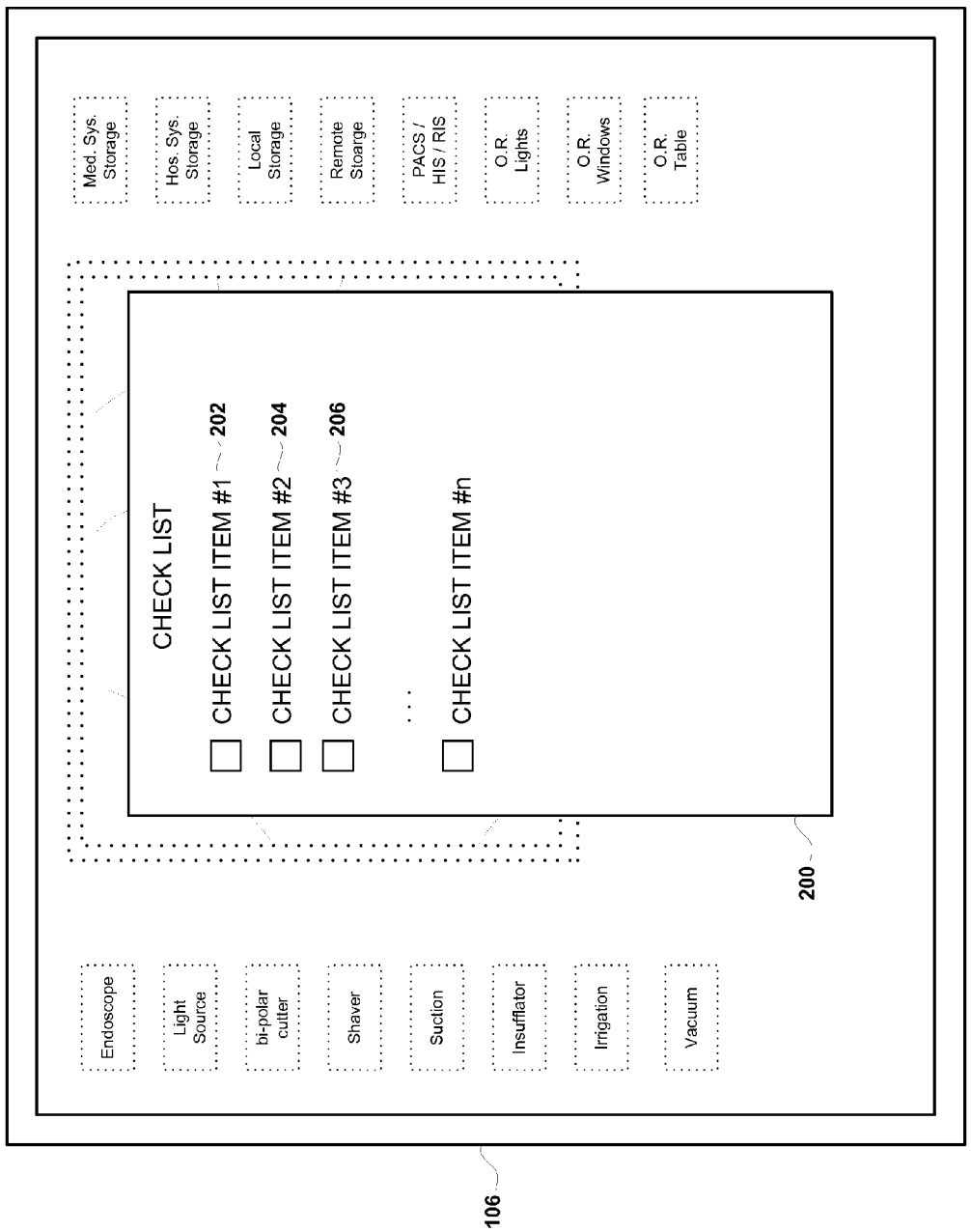
FIG. 16 is an illustration of the touchscreen according to the embodiment of FIG. 2.
Figure 17:
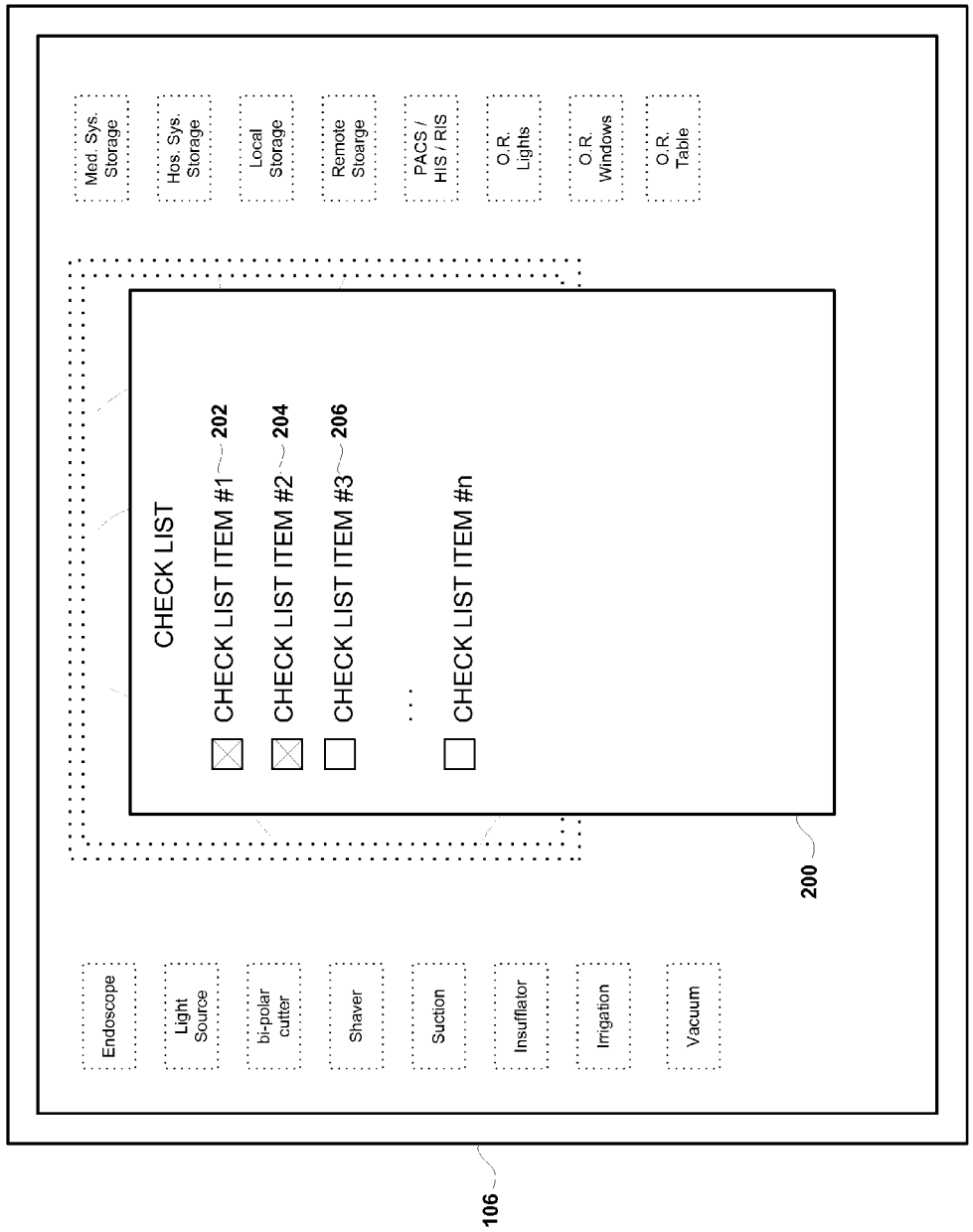
FIG. 17 is an illustration of the touchscreen according to the embodiment of FIG. 2.

FIGS. 16 and 17 illustrate yet another embodiment of the present invention in which a checklist 200 is displayed on front panel 130 of touchscreen 106. The checklist 200 may comprise a number of check list items (202, 204, 206 . . . etc.) that must be completed prior to allowing the user to have access to touchscreen 106 and operating room control system 100. As the checklist items are completed, the user may check the items off on the list as indicated at FIG. 17.

The checklist items can comprise any number of checklist items that must be completed prior to or prior to continuing with a surgical procedure. For example, the checklist items could comprise a checklist of the procedure(s) to be performed and may be checked off as the surgery proceeds. Additionally, the checklist items could comprise a check of all the tools, equipment, devices and so on prior to the procedure. It is understood that multiple checklists may be used, some in advance of the procedure during the set up of the operating room for the procedure, some just prior to the procedure with all the medical staff in the operating room, some during the procedure to ensure that each and every step of the procedure is accounted for, all the medical tools and devices are accounted for and that no steps were omitted.

These checklists can be generated and required by the hospital administration. Additional checklists can be generated that are customized by the surgeon performing the procedure. In any event, the checklists help to ensure that complete, safe, efficient treatments are performed. The checklists also provide for documentation of the procedure as certain items are checked off as the procedure advances.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An operating room control system comprising:
a computer having a network connection;
an operating room system interface coupled to said computer;
a storage accessible by said computer;
an endoscope generating a video output, said endoscope coupled to said operating room system interface;
at least one medical tool coupled to said operating room system interface;
at least one piece of medical equipment coupled to said operating room system interface;
a touchscreen coupled to said operating room system interface;
a surgical monitor coupled to said operating room system interface;
wherein software executes on said computer to present icons on said touchscreen associated with: said endoscope, said storage, said at least one medical tool, and said at least one piece of medical equipment, such that the icons allow for control of the devices and equipment associated therewith;
wherein the video output is displayed on said touchscreen and said surgical monitor; and
wherein the operating room control system is soft configurable such that the icons and the video output are configured and presented on said touchscreen based upon a user's defined configuration.

2. The operating room control system according to claim 1 wherein the video output is configured and presented on said surgical monitor based upon a user's defined configuration.

3. The operating room control system according to claim 1 wherein said at least one medical tool comprises a plurality of medical tools, where each tool has an icon associated therewith and the medical tool icons are configured and presented on said touchscreen based upon a user's defined configuration.

4. The operating room control system according to claim 3 wherein the plurality of medical tools is selected from the group consisting of: catheterization devices, bipolar cutting devices, rotating cutting devices, lasers, cell collection devices, suction devices and combinations thereof.

5. The operating room control system according to claim 1 wherein said at least one piece of medical equipment comprises a plurality of medical equipment, where each piece of equipment has an icon associated therewith and the medical equipment icons are configured and presented on said touchscreen based upon a user's defined configuration.

6. The operating room control system according to claim 5 wherein the plurality of medical equipment, is selected from the group consisting of: insufflation equipment, irrigation equipment, vacuum equipment and combinations thereof.

7. The operating room control system according to claim 1 further comprising at least one piece of operating room equipment coupled to said operating room system interface, where said at least one piece of operating room equipment has an icon associated therewith that is configured and presented on said touchscreen based upon a user's defined configuration.

8. The operating room control system according to claim 7 wherein said at least one piece of operating room equipment comprises a plurality of operating room equipment selected from the group consisting of: hospital information systems, image storage systems, lights, blinds, shades, table and combinations thereof.

9. The operating room control system according to claim 1 wherein said storage comprises a plurality of storage devices where each storage device has an icon associated therewith and the storage device icons are configured and presented on said touchscreen based upon a user's defined configuration.

10. The operating room control system according to claim 9 wherein the plurality of storage devices is selected from the group consisting of: solid state hard drives, magnetic hard drives, optical devices, removable storage devices and combinations thereof.

11. The operating room control system according to claim 9 wherein routing of the video output to a storage device is performed by activating the endoscope icon on said touchscreen and then activating one of the storage device icons on said touchscreen such that the video output is routed to the storage device associated with the activated storage device icon.

12. The operating room control system according to claim 11 wherein when the activated storage device icon is activated a second time, the saving of the video output to the selected storage device is interrupted.

13. The operating room control system according to claim 9 wherein a plurality of storage devices is associated with a single icon presented on said touchscreen.

14. The operating room control system according to claim 9 wherein the system is configured according to a user's preferences to automatically route and save the video output to one of the plurality of storage devices and the video output is routed and saved on a second one of the plurality of storage devices only upon activation of an icon associated with the second one of the plurality of storage devices.

15. The operating room control system according to claim 1 wherein when an icon presented on said touchscreen is activated, the icon visibly changes so as to indicate to the user that the device associated with the icon is activated.

16. The operating room control system according to claim 15 wherein the change to the icon comprises a change in the color of the icon.

17. The operating room control system according to claim 15 wherein the change to the icon comprises an alphanumeric indication over the icon indicating a setting of the device associated with the icon.

18. The operating room control system according to claim 17 wherein when the icon is activated a control interface is displayed on said touchscreen such that the user can adjust a setting of the device associated with the icon and upon changing the setting, the control interface is removed from said touchscreen and the changed setting is displayed on the icon associated with the device to which the setting was changed.

19. The operating room control system according to claim 1 wherein the user retrieves a saved medical image and the medical image is presented on said touchscreen and said surgical monitor based upon the user's defined configuration.

20. The operating room control system according to claim 1 further comprising a checklist presented on said touchscreen wherein the system is locked such that the checklist must be completed prior to the system unlocking.

21. The operating room control system according to claim 20 wherein said touchscreen comprises a first touchscreen and the system further comprises a second touchscreen positioned outside of the sterile environment, said second touchscreen coupled to said operating room system interface and providing all the functionality of said first touchscreen.

22. The operating room control system according to claim 21 herein the checklist is presented on both said first and second touchscreens.

23. The operating room control system according to claim 22 further comprising a third touchscreen presenting thereon, patient vital signs, medical equipment icons for controlling selected medical equipment icons, patient information icons for accessing selected patient information, and medical equipment interfaces indicating current settings of associated medical equipment.

24. The operating room control system according to claim 23 wherein the checklist is presented on said first, second and third touchscreens.

25. The operating room control system according to claim 1 further comprising an unlocking/locking mechanism presented on said touchscreen such that when the user activates the unlocking/locking mechanism, said touchscreen is selectively unlocked so that the user can manually adjust the positioning of the video output and icons on said touchscreen and upon activation of the unlockingilocking mechanism a second time, the position of the video output and icons on said touchscreen is locked.

26. The operating room control system according to claim 1 further comprising a system lock and an input device such that the system will not unlock until an input is received that is within a predetermined acceptable range.

27. An operating room control system comprising:
a computer having a network connection;
an operating room system interface coupled to said computer;
a plurality of storage devices accessible by said computer;
an endoscope generating a video output, said endoscope coupled to said operating room system interface;
at least one medical tool coupled to said operating room system interface;
a plurality of medical equipment coupled to said operating room system interface;
a touchscreen coupled to said operating room system interface;
a surgical monitor coupled to said operating room system interface;
wherein software executes on said computer to present icons on said touchscreen associated with: said endoscope, said plurality of storage devices, and said plurality of medical equipment, such that the icons allow for control of the devices and equipment associated therewith;
wherein the video output is displayed on said touchscreen and said surgical monitor; and
wherein the operating room control system is soft configurable such that the icons and the video output are configured and presented on said touchscreen and said surgical monitor based upon a user's defined configuration.

28. The operating room control system according to claim 27 wherein said at least one medical tool comprises a plurality of medical tools selected from the group consisting of: catheterization devices, bi-polar cutting devices, rotating cutting devices, cell collection devices, suction devices and combinations thereof.

29. The operating room control system according to claim 27 wherein said plurality of medical equipment is selected from the group consisting of: insufflations equipment, irrigation equipment, vacuum equipment and combinations thereof.

30. The operating room control system according to claim 27 further comprising a plurality of operating room equipment coupled to said operating room system interface, and said plurality of operating room equipment has at least one icon associated therewith and presented on said touchscreen, said plurality of operating room equipment selected from the group consisting of: hospital information systems, image storage systems, lights, blinds, shades and combinations thereof.

31. The operating room control system according to claim 27 wherein routing of the video output to a selected storage device is performed by activating the endoscope icon on said touchscreen and then activating one of the storage device icons on said touchscreen such that the video output is routed to the storage device associated with the activated storage device icon.

32. The operating room control system according to claim 31 wherein when the activated storage device icon is activated a second time, the saving of the video output to the selected storage device is interrupted.

33. The operating room control system according to claim 31 wherein the system is configured according to a user's preferences to automatically route and save the video output to one of the plurality of storage devices and the video output is routed and saved on a second one of the plurality of storage devices only upon activation of an icon associated with the second one of the plurality of storage devices.

34. The operating room control system according to claim 27 wherein when an icon presented on said touchscreen is activated, the icon visibly changes so as to indicate to the user that the device associated with the icon is activated.

35. The operating room control system according to claim 34 wherein the change to the icon comprises a change in the color of the icon.

36. The operating room control system according to claim 34 wherein the change to the icon comprises an alphanumeric indication over the icon indicating a setting of the device associated with the icon.

37. The operating room control system according to claim 36 wherein when the icon is activated a control interface is displayed on said touchscreen such that the user can adjust a setting of the device associated with the icon and upon changing the setting, the control interface is removed from said touchscreen and the changed setting is displayed on the icon associated with the device to which the setting was changed.

38. The operating room, control system according to claim 27 further comprising a checklist presented on said touchscreen wherein the system is locked such that the checklist must be completed prior to the system unlocking.

39. The operating room control system according to claim 38 wherein said touchscreen comprises a first touchscreen and the system further comprises a second touchscreen positioned outside of the sterile environment, said second touchscreen coupled to said operating room system interface and providing all the functionality of said first touchscreen.

40. The operating room control system according to claim 39 wherein the checklist is presented on both said first and second touchscreens.

41. The operating room control system according to claim 40 further comprising a third touchscreen presenting thereon, patient vital signs, medical equipment icons for controlling selected medical equipment icons, patient information icons for accessing selected patient information, and medical equipment interfaces indicating current settings of associated medical equipment.

42. The operating room control system according to claim 4 wherein the checklist is presented on said first, second and third touchscreens.

43. The operating room control system according to claim 1 further comprising an unlocking/locking mechanism presented on said touchscreen such that when the user activates the unlocking/locking mechanism, said touchscreen is selectively unlocked so that the user can manually adjust the positioning of the video output and icons on said touchscreen and upon activation of the unlocking/locking mechanism a second time, the position of the video output and icons on said touchscreen is locked.

* * * * *